United States Patent
Afar et al.

(10) Patent No.: US 6,652,859 B1
(45) Date of Patent: Nov. 25, 2003

(54) PTANS: TESTIS SPECIFIC PROTEINS EXPRESSED IN PROSTATE CANCER

(75) Inventors: Daniel E. Afar, Pacific Palisades, CA (US); Rene S. Hubert, Los Angeles, CA (US); Arthur B. Raitano, Los Angeles, CA (US); Stephen Chappell Mitchell, Santa Monica, CA (US)

(73) Assignee: Agensys, Inc., Santa Monica, CA (US)

( * ) Notice: Subject to any disclaimer, the term of this patent is extended or adjusted under 35 U.S.C. 154(b) by 0 days.

(21) Appl. No.: 09/409,938

(22) Filed: Sep. 30, 1999

Related U.S. Application Data

(60) Provisional application No. 60/129,518, filed on Apr. 14, 1999, provisional application No. 60/113,229, filed on Dec. 21, 1998, provisional application No. 60/102,910, filed on Oct. 2, 1998, and provisional application No. 60/102,556, filed on Sep. 30, 1998.

(51) Int. Cl.[7] .............................................. A61K 39/00
(52) U.S. Cl. .................... 424/185.1; 530/326; 530/350; 424/277.1
(58) Field of Search ................................ 530/300, 350, 530/326; 424/277.1

(56) References Cited

FOREIGN PATENT DOCUMENTS

| WO | WO 98/16628 | 4/1998 |
|---|---|---|
| WO | WO 200166752 A2 * | 9/2001 |

OTHER PUBLICATIONS

Bodey, B, et al, 2000, Failure of cancer vaccines: the significant limitations of this approach to immunotherapy, Anticancer Research, vol. 20, pp. 2665–2676.*
Arceci, RJ, 1998, The potential for antitumor vaccination in acute myelogenous leukemia, Journal of Molecular Medicine, vol. 76, pp. 80–93.*
Lee, K–H, et al, 1999, Increased vaccine–specific T cell frequency after peptide–based vaccination correlates with increased susceptibility to in vitro stimulation but does not lead to tumor regression, Journal of Immunology, vol. 163, pp. 6292–6300.*
Zaks, TZ, et al, 1998, Immunization with a peptide epitope (p369–377) from HER–2/neu leads to peptide–specific cytotoxic T lymphocytes that fail to recognize HER–2/neu+ tumors, Cancer Research, vol. 58, pp. 4902–4908.*
Gura, T, 1997, Systems for identifying drugs are often faulty, Science, vol. 278, pp. 1041–1042.*
Janlanko, H, et al, 1978, Early increase of serum alpha–fetoprotein in spontaneous hepatocarcinogenesis in mice, International Journal of Cancer, vol. 21, pp. 453–459.*
Timmerman, JM, et al, 1999, Dendritic cell vaccines for cancer immunotherapy, Annual Review of Medicine, vol. 50, pp. 507–529.*
Ezzell, C, 1995, Cancer "vaccines": an idea whose time has come?, Journal of NIH Research, vol. 7, pp. 46–49.*
Splitler, LE, 1995, Cancer vaccines: the interferon analogy, Cancer Biotherapy, vol. 10, No. 1, pp. 1–3.*
Boon, T, 1992, Toward a genetic analysis of tumor rejection antigens, Advances in Cancer Research, vol. 58, pp. 177–210.*
Lee, C, et al, 1993, In vivo and in vitro approaches to study metastasis in human prostatic cancer, Cancer and Metastasis Reviews, vol. 12, pp. 21–28.*
Hoomes, EH, 2001, PSMA specific antibodies and their diagnositic and therapeutic use, Expert Opinion on Investigational Drugs, vol. 10, No. 3, pp. 511–519.*
Bowie, JU, et al, 1990, Deciphering the message in protein sequences: tolerance to amino acid substitutions, Science, vol. 247, pp. 1306–1310.*
Burgess, WH, et al, 1990, Possible dissociation of the heparin–binding and mitogenic activities of heparin–binding (acidic fibroblast) growth factor–1, J Cell Biology, vol. 111, pp. 2129–2138.*
Lazar, E, et al, 1988 Transforming growth factor alpha: mutation of aspartic acid 47 and leucine 48 results in different biological activities, Molecular and Cellular Biology, vol. 8, pp. 1247–1252.*
Hillier, L, et al, 1997 Database Genbank Accession No. AA393260, zt75c07.r1 Soares_NHT Homo sapiens CDNA clone IMAGE: 728172 5', mRNA sequence.*
National Cancer Institute —Cancer Genome Anatomy Project (NCI–CGAP), 1997, Database Genbank Accession No. AW134538, UI–H–BI1–abv–a–03–UI.s1 NCI_CGAP_Sub3 Homo sapiens CDNA clone IMAGE: 2712869 3', mRNA sequence.*
DeSmet, C. et al., "Human Testis Homo Sapiens cDNA Clone TDP3.12b," Database EMBL Sequences Online, XP–0021355705, Accession No. AF012390, Jan. 7, 1998.
DeSmet, C. et al., "Identification of Human Testis–Specific Transcripts and Analysis of Their Expression in Tumor Cells," XP–002135703, Biochem. Biophys. Res. Comm., 1997, vol. 241:653–657.
Klein, K.A. et al., "Progression of Metastatic Human Prostate Cancer to Androge Independence in Immunodeficient SCID Mice," XP–002135704, Nature Medicine, 1997, 3(4):402–408.
R.K. Wilson, Aug. 12, 1997, dbEST Id: 1034724, GenBank Acc: AA393260.

(List continued on next page.)

*Primary Examiner*—Anthony C. Caputa
*Assistant Examiner*—Stephen L. Rawlings
(74) *Attorney, Agent, or Firm*—Morrison & Foerster LLP

(57) ABSTRACT

Novel testis-specific genes and encoded proteins (PTANs) are described. PTANs are over-expressed in prostate cancer. The nucleotide and amino acid sequences of three distinct PTAN isoforms, designated PTAN-1, PTAN-2 and PTAN-3 are provided. The PTANs show no homology to any known gene. The testis-specific expression profile of PTAN in normal adult tissues, combined with the over-expression observed in prostate tumor xenografts, suggests that PTAN may be aberrancy over-expressed in at least some prostate cancers, and thus may be a useful diagnostic and/or therapeutic target for prostate cancers.

6 Claims, 20 Drawing Sheets

OTHER PUBLICATIONS

R.K. Wilson, Aug. 12, 1997, dbEST Id: 1040150, GenBank Acc: AA398518.
R. Strausberg, Jun. 22, 1998, dbEST Id: 1765825, GenBank Acc: AI026927.
R. K. Wilson, Jun. 3, 1997, dbEST Id: 1090471, GenBankAcc: AA446177.
R. Strausberg, Feb. 13, 1999, dbEST Id: 2122167, GenBank Acc: AI338425.
R. Strausberg, Oct. 28, 1998, dbEST Id: 1897559, GenBank Acc: AI138893.
R.K. Wilson, Jun. 3, 1997, dbEST Id: 1090367, GenBank: AA446073.
R. Strausberg, Dec. 17, 1999, dbEST Id: 2480550, GenBank Acc: AI651906.
R.K. Wilson, Nov. 9, 1997, dbEST Id: 1060606, GenBank Acc: AA416959.
R. K. Wilson, Oct. 16, 1997, dbEST Id: 1074612, GenBank Acc: AA429917.
R. Strausberg, Dec. 19, 1999, dbEST Id: 2724127, GenBak Acc: AI769054.
R. K. Wilson, Nov. 9, 1997, dbEST Id: 1114669, GenBank Acc: AA470046.
R.K. Wilson, Oct. 16, 1997, dbEST Id: 1074578, GenBank Acc: AA 429883.
R.K. Wilson, Nov. 9, 1997, dbEST Id: 1065207, GenBank Acc: AA421199.
R. Strausberg, Dec. 17, 1999, dbEST Id: 2483412, GenBank Acc: AI654768.
R. K. Wilson, Nov. 9, 1997, dbEST Id: 1061110, GenBank Acc: AA416548.
R. Strausberg, Dec. 29, 1998, dbEST Id: 1480429, GenBank Acc: AA758686.
R. Strausberg, Aug. 21, 1997, dbEST Id: 868031, GenBank Acc: AA229169.
R. Strausberg, Jan. 12, 1999, dbEST Id: 1425681, GenBank Acc: AA718929.
R.K. Wilson, Mar. 2, 1998, dbEST Id: 1306682, GenBank Acc: AA608981.
R. Strausberg, Aug. 21, 1997, dbEST Id: 868046, GenBank Acc: AA229204.
R.K. Wilson, Aug. 12, 1997, dbEST Id: 1034408, GenBank Acc: AA393102.
C. De Smet, Apr. 23, 1998, dbEST Id: 1662929, GenBank Acc: AF012352.
Klein et al., Nature Med. (1997) 3:402–408.
Morton and Myszka, Methods in Enzymology (1998) 295:268.
Muller et al., MCB (1991) 11:1785.
Pemberton et al., J. of Histochemistry and Cytochemistry (1997) 45:1697–1706.
Welch et al., Int. J. Cancer (1989) 43:449–457.
Welford, Opt. Quant. Elect. (1991) 23:1.

* cited by examiner

```
                 10              19              28              37              46              55
5' GCC AGG AAG TTT GAC CGC GCT GCC ATG CCG AAC CGT AAG CCC AGC CGG AAT GCT
   --- --- --- --- --- --- --- --- --- --- --- --- --- --- --- --- --- ---
    A   R   K   F   D   R   A   A   M   P   N   R   K   A   S   R   N   A 64              73              82              91             100             109
   TAC TAT TTC TTC GTG CAG GAG AAG ATC CCC GAA CTA CGG CGA CGA GGC CTG CCT
   --- --- --- --- --- --- --- --- --- --- --- --- --- --- --- --- --- ---
    Y   Y   F   F   V   Q   E   K   I   P   E   L   R   R   R   G   L   P 118             127             136             145             154             163
   GTG GCT CGC GTT GCT GAT GCC ATC CCT TAC TGC TCC TCA GAC TGG GCG CTT CTG
   --- --- --- --- --- --- --- --- --- --- --- --- --- --- --- --- --- ---
    V   A   R   V   A   D   A   I   P   Y   C   S   S   D   W   A   L   L 172             181             190             199             208             217
   AGG GAG GAA GAA AAG GAG AAA TAC GCA GAA ATG GCT CGA GAA TGG AGG GCC GCT
   --- --- --- --- --- --- --- --- --- --- --- --- --- --- --- --- --- ---
    R   E   E   E   K   E   K   Y   A   E   M   A   R   E   W   R   A   A 226             235             244             253             262             271
   CAG GGA AAG GAC CCT GGG CCC TCA GAG AAG CAG AAA CCT GTT TTC ACA CCA CTG
   --- --- --- --- --- --- --- --- --- --- --- --- --- --- --- --- --- ---
    Q   G   K   D   P   G   P   S   E   K   Q   K   P   V   F   T   P   L 280             289             298             307             316             325
   AGG AGG CCA GGC ATG CTT GTA CCA AAG CAG AAT GTT TCA CCT CCA GAT ATG TCA
   --- --- --- --- --- --- --- --- --- --- --- --- --- --- --- --- --- ---
    R   R   P   G   M   L   V   P   K   Q   N   V   S   P   P   D   M   S 334             343             352             361             370             379
   GCT TTG TCT TTA AAA GGT GAT CAA GCT CTC CTT GGA GGC ATT TTT TAT TTT TTG
   --- --- --- --- --- --- --- --- --- --- --- --- --- --- --- --- --- ---
    A   L   S   L   K   G   D   Q   A   L   L   G   G   I   F   Y   F   L 388             397             406             415             424             433
   AAC ATT TTT AGC CAT GGC GAG CTA CCT CCT CAT TGT GAA CAG CGC TTC CTC CCT
   --- --- --- --- --- --- --- --- --- --- --- --- --- --- --- --- --- ---
    N   I   F   S   H   G   E   L   P   P   H   C   E   Q   R   F   L   P 442             451             460             469             478             487
   TGT GAA ATT GGC TGT GTT AAG TAT TCT CTC CAA GAA GGT ATT ATG GCA GAT TTC
   --- --- --- --- --- --- --- --- --- --- --- --- --- --- --- --- --- ---
    C   E   I   G   C   V   K   Y   S   L   Q   E   G   I   M   A   D   F 496             505             514             523             532             541
   CAC AGT TTT ATA AAT CCT GGT GAA ATT CCA CGA GGA TTT CGA TTT CAT TGT CAG
   --- --- --- --- --- --- --- --- --- --- --- --- --- --- --- --- --- ---
    H   S   F   I   N   P   G   E   I   P   R   G   F   R   F   H   C   Q 550             559             568             577             586             595
   GCT GCA AGT GAT TCT AGT CAC AAG ATT CCT ATT TCA AAT TTT GAA CGT GGG CAT
   --- --- --- --- --- --- --- --- --- --- --- --- --- --- --- --- --- ---
    A   A   S   D   S   S   H   K   I   P   I   S   N   F   E   R   G   H 604             613             622             631             640             649
   AAC CAA GCA ACT GTG TTA CAA AAC CTT TAT AGA TTT ATT CAT CCC AAC CCA GGG
   --- --- --- --- --- --- --- --- --- --- --- --- --- --- --- --- --- ---
    N   Q   A   T   V   L   Q   N   L   Y   R   F   I   H   P   N   P   G 658             667             676             685             694             703
   AAC TGG CCA CCT ATC TAC TGC AAG TCT GAT GAT AGA ACC AGA GTC AAC TGG TGT
   --- --- --- --- --- --- --- --- --- --- --- --- --- --- --- --- --- ---
    N   W   P   P   I   Y   C   K   S   D   D   R   T   R   V   N   W   C 712             721             730             739             748             757
   TTG AAG CAT ATG GCA AAG GCA TCA GAA ATC AGG CAA GAT CTA CAA CTT CTC ACT
   --- --- --- --- --- --- --- --- --- --- --- --- --- --- --- --- --- ---
    L   K   H   M   A   K   A   S   E   I   R   Q   D   L   Q   L   L   T
```

FIG. 1A

```
          766           775           784           793           802           811
GTA GAG GAC CTT GTA GTG GGG ATC TAC CAA CAA AAA TTT CTC AAG GAG CCC TCT
 V   E   D   L   V   V   G   I   Y   Q   Q   K   F   L   K   E   P   S 820           829           838           847           856           865
AAG ACT TGG ATT CGA AGC CTC CTA GAT GTG GCC ATG TGG GAT TAT TCT AGC AAC
 K   T   W   I   R   S   L   L   D   V   A   M   W   D   Y   S   S   N 874           883           892           901           910           919
ACA AGG TGC AAG TGG CAT GAA GAA AAT GAT ATT CTC TTC TGT GCT TTA GCT GTT
 T   R   C   K   W   H   E   E   N   D   I   L   F   C   A   L   A   V 928           937           946           955           964           973
TGC AAG AAG ATT GCG TAC TGC ATC AGT AAT TCT CTG GCC ACT CTC TTT GGA ATC
 C   K   K   I   A   Y   C   I   S   N   S   L   A   T   L   F   G   I 982           991          1000          1009          1018          1027
CAG CTC ACA GAG GCT CAT GTA CCA CTA CAA GAT TAT GAG GCC AGC AAT AGT GTG
 Q   L   T   E   A   H   V   P   L   Q   D   Y   E   A   S   N   S   V 1036          1045          1054          1063          1072          1081
ACA CCC AAA ATG GTT GTA TTG GAT GCA GGG CGT TAC CAG AAG CTA AGG GTT GGG
 T   P   K   M   V   V   L   D   A   G   R   Y   Q   K   L   R   V   G 1090          1099          1108          1117          1126          1135
AGT TCA GGA TTC TCT CAT TTC AAC TCT TCT AAT GAG GAA CAA AGA TCA AAC ACA
 S   S   G   F   S   H   F   N   S   S   N   E   E   Q   R   S   N   T 1144          1153          1162          1171          1180          1189
CCC ATT GGT GAC TAC CCA TCT AGG GCA AAA ATT TCT GGC CAA AAC AGC AGC GTT
 P   I   G   D   Y   P   S   R   A   K   I   S   G   Q   N   S   S   V 1198          1207          1216          1225          1234          1243
CGG GGA AGA GGA ATT ACC CGC TTA CTA GAG AGC ATT TCC AAT TCT TCC AGC AAT
 R   G   R   G   I   T   R   L   L   E   S   I   S   N   S   S   S   N 1252          1261          1270          1279          1288          1297
ATC CAC AAA TTC TCC AAC TGT GAC ACT TCA CTC TCA CCT TAC ATG TCC CAA AAA
 I   H   K   F   S   N   C   D   T   S   L   S   P   Y   M   S   Q   K 1306          1315          1324          1333          1342          1351
GAT GGA TAC AAA TCT TTC TCT TCC TTA TCT TAA TGA TGG TAC TCT TTT CAA TTT
 D   G   Y   K   S   F   S   S   L   S   *   *

1360          1369          1378          1387          1396          1405
CTG AAA ACA GTA ACA GGC CCA ACT TCC TTC TTA CTA CAG TCA TAT TAA ACA GAT 1414          1423          1432          1441          1450          1459
CAC ATC AAT GAC AAA TGT CAC TAC TAT AAA AAC TAC TTA ATT TGT AAG GAA ATT 1468          1477          1486          1495          1504          1513
GTT TCA TAG ATT TAA AAA AAT TGT GGT TGG AGA GCA TCT TGG CAT TTG TGC TTT 1522          1531          1540          1549          1558          1567
TTT TCT TGA GGG ATT GTT CTG CTT CCT GGC TGT ATG ATG GGT ATA TCA TTA AAG 1576          1585          1594          1603          1612          1621
TTT GGA GTC CTA TAT GAA CAA AAC TGA CAT TTT TAG AGT TGT ACT TTT GGG AAT 1630          1639          1648          1657          1666          1675
GTT ATA GAT TGA TCA TTC TTT CTC CTG ATA ATA AAG GTA TTG AAT ATC TGT TAA

1684
AAA AAA AAA AAA AAA 3'
```

FIG. 1B

```
                    9              18             27             36             45             54
5' GCC CGG CGA GGG CGC CGG TGC TTT GTT CTG TCT GAG GCC AGG AAG TTT GAC CGC
   --- --- --- --- --- --- --- --- --- --- --- --- --- --- --- --- --- ---
    A   R   R   G   R   R   C   F   V   L   S   E   A   R   K   F   D   R 63             72             81             90             99            108
   GCT GCC ATG CCG AAC CGT AAG GCC AGC CGG AAT GCT TAC TAT TTC TTC GTG CAG
   --- --- --- --- --- --- --- --- --- --- --- --- --- --- --- --- --- ---
    A   A   M   P   N   R   K   A   S   R   N   A   Y   Y   F   F   V   Q 117            126            135            144            153            162
   GAG AAG ATC CCC GAA CTA CGG CGA CGA GGC CTG CCT GTG GCT CGC GTT GCT GAT
   --- --- --- --- --- --- --- --- --- --- --- --- --- --- --- --- --- ---
    E   K   I   P   E   L   R   R   R   G   L   P   V   A   R   V   A   D 171            180            189            198            207            216
   GCC ATC CCT TAC TGC TCC TCA GAC TGG GCG AAA CCT GTT TTC ACA CCA CTG AGG
   --- --- --- --- --- --- --- --- --- --- --- --- --- --- --- --- --- ---
    A   I   P   Y   C   S   S   D   W   A   K   P   V   F   T   P   L   R 225            234            243            252            261            270
   AGG CCA GGC ATG CTT GTA CCA AAG CAG AAT GTT TCA CCT CCA GAT ATG TCA GCT
   --- --- --- --- --- --- --- --- --- --- --- --- --- --- --- --- --- ---
    R   P   G   M   L   V   P   K   Q   N   V   S   P   P   D   M   S   A 279            288            297            306            315            324
   TTG TCT TTA AAA GGT GAT CAA GCT CTC CTT GGA GGC ATT TTT TAT TTT TTG AAC
   --- --- --- --- --- --- --- --- --- --- --- --- --- --- --- --- --- ---
    L   S   L   K   G   D   Q   A   L   L   G   G   I   F   Y   F   L   N 333            342            351            360            369            378
   ATT TTT AGC CAT GGC GAG CTA CCT CCT CAT TGT GAA CAG CGC TTC CTC CCT TGT
   --- --- --- --- --- --- --- --- --- --- --- --- --- --- --- --- --- ---
    I   F   S   H   G   E   L   P   P   H   C   E   Q   R   F   L   P   C 387            396            405            414            423            432
   GAA ATT GGC TGT GTT AAG TAT TCT CTC CAA GAA GGT ATT ATG GCA GAT TTC CAC
   --- --- --- --- --- --- --- --- --- --- --- --- --- --- --- --- --- ---
    E   I   G   C   V   K   Y   S   L   Q   E   G   I   M   A   D   F   H 441            450            459            468            477            486
   AGT TTT ATA AAT CCT GGT GAA ATT CCA CGA GGA TTT CGA TTT CAT TGT CAG GCT
   --- --- --- --- --- --- --- --- --- --- --- --- --- --- --- --- --- ---
    S   F   I   N   P   G   E   I   P   R   G   F   R   F   H   C   Q   A 495            504            513            522            531            540
   GCA AGT GAT TCT AGT CAC AAG ATT CCT ATT TCA AAT TTT GAA CGT GGG CAT AAC
   --- --- --- --- --- --- --- --- --- --- --- --- --- --- --- --- --- ---
    A   S   D   S   S   H   K   I   P   I   S   N   F   E   R   G   H   N 549            558            567            576            585            594
   CAA GCA ACT GTG TTA CAA AAC CTT TAT AGA TTT ATT CAT CCC AAC CCA GGG AAC
   --- --- --- --- --- --- --- --- --- --- --- --- --- --- --- --- --- ---
    Q   A   T   V   L   Q   N   L   Y   R   F   I   H   P   N   P   G   N 603            612            621            630            639            648
   TGG CCA CCT ATC TAC TGC AAG TCT GAT GAT AGA ACC AGA GTC AAC TGG TGT TTG
   --- --- --- --- --- --- --- --- --- --- --- --- --- --- --- --- --- ---
    W   P   P   I   Y   C   K   S   D   D   R   T   R   V   N   W   C   L 657            666            675            684            693            702
   AAG CAT ATG GCA AAG GCA TCA GAA ATC AGG CAA GAT CTA CAA CTT CTC ACT GTA
   --- --- --- --- --- --- --- --- --- --- --- --- --- --- --- --- --- ---
    K   H   M   A   K   A   S   E   I   R   Q   D   L   Q   L   L   T   V 711            720            729            738            747            756
   GAG GAC CTT GTA GTG GGG ATC TAC CAA CAA AAA TTT CTC AAG GAG CCC TCT AAG
   --- --- --- --- --- --- --- --- --- --- --- --- --- --- --- --- --- ---
    E   D   L   V   V   G   I   Y   Q   Q   K   F   L   K   E   P   S   K
```

FIG. 2A

```
      765           774            783           792           801           810
ACT TGG ATT CGA AGC CTC CTA GAT GTG GCC ATG TGG GAT TAT TCT AGC AAC ACA
--- --- --- --- --- --- --- --- --- --- --- --- --- --- --- --- --- ---
 T   W   I   R   S   L   L   D   V   A   M   W   D   Y   S   S   N   T 819           828            837           846           855           864
AGG TGC AAG TGG CAT GAA GAA AAT GAT ATT CTC TTC TGT GCT TTA GCT GTT TGC
--- --- --- --- --- --- --- --- --- --- --- --- --- --- --- --- --- ---
 R   C   K   W   H   E   E   N   D   I   L   F   C   A   L   A   V   C 873           882            891           900           909           918
AAG AAG ATT GCG TAC TGC ATC AGT AAT TCT CTG GCC ACT CTC TTT GGA ATC CAG
--- --- --- --- --- --- --- --- --- --- --- --- --- --- --- --- --- ---
 K   K   I   A   Y   C   I   S   N   S   L   A   T   L   F   G   I   Q 927           936            945           954           963           972
CTC ACA GAG GCT CAT GTA CCA CTA CAA GAT TAT GAG GCC AGC AAT AGT GTG ACA
--- --- --- --- --- --- --- --- --- --- --- --- --- --- --- --- --- ---
 L   T   E   A   H   V   P   L   Q   D   Y   E   A   S   N   S   V   T 981           990            999          1008          1017          1026
CCC AAA ATG GTT GTA TTG GAT GCA GGG CGT TAC CAG AAG CTA AGG GTT GGG AGT
--- --- --- --- --- --- --- --- --- --- --- --- --- --- --- --- --- ---
 P   K   M   V   V   L   D   A   G   R   Y   Q   K   L   R   V   G   S 1035          1044           1053          1062          1071          1080
TCA GGA TTC TCT CAT TTC AAC TCT TCT AAT GAG GAA CAA AGA TCA AAC ACA CCC
--- --- --- --- --- --- --- --- --- --- --- --- --- --- --- --- --- ---
 S   G   F   S   H   F   N   S   S   N   E   E   Q   R   S   N   T   P 1089          1098           1107          1116          1125          1134
ATT GGT GAC TAC CCA TCT AGG GCA AAA ATT TCT GGC CAA AAC AGC AGC GTT CGG
--- --- --- --- --- --- --- --- --- --- --- --- --- --- --- --- --- ---
 I   G   D   Y   P   S   R   A   K   I   S   G   Q   N   S   S   V   R 1143          1152           1161          1170          1179          1188
GGA AGA GGA ATT ACC CGC TTA CTA GAG AGC ATT TCC AAT TCT TCC AGC AAT ATC
--- --- --- --- --- --- --- --- --- --- --- --- --- --- --- --- --- ---
 G   R   G   I   T   R   L   L   E   S   I   S   N   S   S   S   N   I 1197          1206           1215          1224          1233          1242
CAC AAA TTC TCC AAC TGT GAC ACT TCA CTC TCA CCT TAC ATG TCC CAA AAA GAT
--- --- --- --- --- --- --- --- --- --- --- --- --- --- --- --- --- ---
 H   K   F   S   N   C   D   T   S   L   S   P   Y   M   S   Q   K   D 1251          1260           1269          1278          1287          1296
GGA TAC AAA TCT TTC TCT TCC TTA TCT TAA TGA TGG TAC TCT TTT CAA TTT CTG
--- --- --- --- --- --- --- --- --- --- --- --- --- --- --- --- --- ---
 G   Y   K   S   F   S   S   L   S   *   *

1305          1314           1323          1332          1341          1350
AAA ACA GTA ACA GGC CCA ACT TCC TTC TTA CTA CAG TCA TAT TAA ACA GAT CAC
--- --- --- --- --- --- --- --- --- --- --- --- --- --- --- --- --- ---

1359          1368           1377          1386          1395          1404
ATC AAT GAC AAA TGT CAC TAC TAT AAA AAC TAC TTA ATT TGT AAG GAA ATT GTT
--- --- --- --- --- --- --- --- --- --- --- --- --- --- --- --- --- ---

1413          1422           1431          1440          1449          1458
TCA TAG ATT TTA AAA AAT TGT GGT TGG AGA GCA TCT TGG CAT TTG TGC TTT TTT
--- --- --- --- --- --- --- --- --- --- --- --- --- --- --- --- --- ---

1467          1476           1485          1494          1503          1512
TCT TGA GGG ATT GTT CTG CTT CCT GGC TGT ATG ATG GGT ATA TCA TTA AAG TTT
--- --- --- --- --- --- --- --- --- --- --- --- --- --- --- --- --- ---

1521          1530           1539          1548          1557          1566
GGA GTC CTA TAT GAA CAA AAC TGA CAT TTT TAG AGT TGT ACT TTT GGG AAT GTT
--- --- --- --- --- --- --- --- --- --- --- --- --- --- --- --- --- ---

1575          1584           1593          1602          1611          1620
ATA GAT TGA TCA TTC TTT CTC CTG ATA ATA AAG GTA TTG AAT ATC TGT TAT GAA
--- --- --- --- --- --- --- --- --- --- --- --- --- --- --- --- --- ---

1629          1638
AGG TTA AAA AAA AAA AAA AA 3'
--- --- --- --- --- --- ---
```

FIG. 2B

```
            9              18             27             36             45             54
5' GCG CGG CAC GGG GCG AGC GTC TCC CCG CCG CAG AGC CCG CCG CGC GGG GGA GCT
   --- --- --- --- --- --- --- --- --- --- --- --- --- --- --- --- --- ---
               63             72             81             90             99            108
   CGG CCC GCC GCA CCG CCT CCC GCG CCT CCG CCC CGC CGC CCG CTG CCG CGA CTG
   --- --- --- --- --- --- --- --- --- --- --- --- --- --- --- --- --- ---
              117            126            135            144            153            162
   CCA AAG TTT CTC GGT CAC GTG CTG GCC CCC GGC GGC CCA AAG GAG AAG ATC CCC
   --- --- --- --- --- --- --- --- --- --- --- --- --- --- --- --- --- ---
              171            180            189            198            207            216
   GAA CTA CGG CGA CGA GGC CTG CCT GTG GCT CGC GTT GCT GAT GCC ATC CCT TAC
   --- --- --- --- --- --- --- --- --- --- --- --- --- --- --- --- --- ---
              225            234            243            252            261            270
   TGC TCC TCA GAC TGG GCG CTT CTG AGG GAG GAA GAA AAG GAG AAA TAC GCA GAA
   --- --- --- --- --- --- --- --- --- --- --- --- --- --- --- --- --- ---
              279            288            297            306            315            324
   ATG GCT CGA GAA TGG AGG GCC GCT CAG GGA AAG GAC CCT GGG CCC TCA GAG AAG
   --- --- --- --- --- --- --- --- --- --- --- --- --- --- --- --- --- ---
    M   A   R   E   W   R   A   A   Q   G   K   D   P   G   P   S   E   K 333            342            351            360            369            378
   CAG AAA CCT GTT TTC ACA CCA CTG AGG AGG CCA GGC ATG CTT GTA CCA AAG CAG
   --- --- --- --- --- --- --- --- --- --- --- --- --- --- --- --- --- ---
    Q   K   P   V   F   T   P   L   R   R   P   G   M   L   V   P   K   Q 387            396            405            414            423            432
   AAT GTT TCA CCT CCA GAT ATG TCA GCT TTG TCT TTA AAA GCT CTC CTT GGA GGC
   --- --- --- --- --- --- --- --- --- --- --- --- --- --- --- --- --- ---
    N   V   S   P   P   D   M   S   A   L   S   L   K   A   L   L   G   G 441            450            459            468            477            486
   ATT TTT TAT TTT TTG AAC ATT TTT AGC CAT GGC GAG CTA CCT CCT CAT TGT GAA
   --- --- --- --- --- --- --- --- --- --- --- --- --- --- --- --- --- ---
    I   F   Y   F   L   N   I   F   S   H   G   E   L   P   P   H   C   E 495            504            513            522            531            540
   CAG CGC TTC CTC CCT TGT GAA ATT GGC TGT GTT AAG TAT TCT CTC CAA GAA GGT
   --- --- --- --- --- --- --- --- --- --- --- --- --- --- --- --- --- ---
    Q   R   F   L   P   C   E   I   G   C   V   K   Y   S   L   Q   E   G 549            558            567            576            585            594
   ATT ATG GCA GAT TTC CAC AGT TTT ATA AAT CCT GGT GAA ATT CCA CGA GGA TTT
   --- --- --- --- --- --- --- --- --- --- --- --- --- --- --- --- --- ---
    I   M   A   D   F   H   S   F   I   N   P   G   E   I   P   R   G   F 603            612            621            630            639            648
   CGA TTT CAT TGT CAG GCT GCA AGT GAT TCT AGT CAC AAG ATT CCT ATT TCA AAT
   --- --- --- --- --- --- --- --- --- --- --- --- --- --- --- --- --- ---
    R   F   H   C   Q   A   A   S   D   S   S   H   K   I   P   I   S   N 657            666            675            684            693            702
   TTT GAA CGT GGG CAT AAC CAA GCA ACT GTG TTA CAA AAC CTT TAT AGA TTT ATT
   --- --- --- --- --- --- --- --- --- --- --- --- --- --- --- --- --- ---
    F   E   R   G   H   N   Q   A   T   V   L   Q   N   L   Y   R   F   I 711            720            729            738            747            756
   CAT CCC AAC CCA GGG AAC TGG CCA CCT ATC TAC TGC AAG TCT GAT GAT AGA ACC
   --- --- --- --- --- --- --- --- --- --- --- --- --- --- --- --- --- ---
    H   P   N   P   G   N   W   P   P   I   Y   C   K   S   D   D   R   T 765            774            783            792            801            810
   AGA GTC AAC TGG TGT TTG AAG CAT ATG GCA AAG GCA TCA GAA ATC AGG CAA GAT
   --- --- --- --- --- --- --- --- --- --- --- --- --- --- --- --- --- ---
    R   V   N   W   C   L   K   H   M   A   K   A   S   E   I   R   Q   D
```

FIG. 3A

```
        819           828           837           846           855           864
CTA CAA CTT CTC ACT GTA GAG GAC CTT GTA GTG GGG ATC TAC CAA CAA AAA TTT
--- --- --- --- --- --- --- --- --- --- --- --- --- --- --- --- --- ---
 L   Q   L   L   T   V   E   D   L   V   V   G   I   Y   Q   Q   K   F 873           882           891           900           909           918
CTC AAG GAG CCC TCT AAG ACT TGG ATT CGA AGC CTC CTA GAT GTG GCC ATG TGG
--- --- --- --- --- --- --- --- --- --- --- --- --- --- --- --- --- ---
 L   K   E   P   S   K   T   W   I   R   S   L   L   D   V   A   M   W 927           936           945           954           963           972
GAT TAT TCT AGC AAC ACA AGG TGC AAG TGG CAT GAA GAA AAT GAT ATT CTC TTC
--- --- --- --- --- --- --- --- --- --- --- --- --- --- --- --- --- ---
 D   Y   S   S   N   T   R   C   K   W   H   E   E   N   D   I   L   F 981           990           999           1008          1017          1026
TGT GCT TTA GCT GTT TGC AAG AAG ATT GCG TAC TGC ATC AGT AAT TCT CTG GCC
--- --- --- --- --- --- --- --- --- --- --- --- --- --- --- --- --- ---
 C   A   L   A   V   C   K   K   I   A   Y   C   I   S   N   S   L   A 1035          1044          1053          1062          1071          1080
ACT CTC TTT GGA ATC CAG CTC ACA GAG GCT CAT GTA CCA CTA CAA GAT TAT GAG
--- --- --- --- --- --- --- --- --- --- --- --- --- --- --- --- --- ---
 T   L   F   G   I   Q   L   T   E   A   H   V   P   L   Q   D   Y   E 1089          1098          1107          1116          1125          1134
GCC AGC AAT AGT GTG ACA CCC AAA ATG GTT GTA TTG GAT GCA GGG CGT TAC CAG
--- --- --- --- --- --- --- --- --- --- --- --- --- --- --- --- --- ---
 A   S   N   S   V   T   P   K   M   V   V   L   D   A   G   R   Y   Q 1143          1152          1161          1170          1179          1188
AAG CTA AGG GTT GGG AGT TCA GGA TTC TCT CAT TTC AAC TCT TCT AAT GAG GAA
--- --- --- --- --- --- --- --- --- --- --- --- --- --- --- --- --- ---
 K   L   R   V   G   S   S   G   F   S   H   F   N   S   S   N   E   E 1197          1206          1215          1224          1233          1242
CAA AGA TCA AAC ACA CCC ATT GGT GAC TAC CCA TCT AGG GCA AAA ATT TCT GGC
--- --- --- --- --- --- --- --- --- --- --- --- --- --- --- --- --- ---
 Q   R   S   N   T   P   I   G   D   Y   P   S   R   A   K   I   S   G 1251          1260          1269          1278          1287          1296
CAA AAC AGC AGC GTT CGG GGA AGA GGA ATT ACC CGC TTA CTA GAG AGC ATT TCC
--- --- --- --- --- --- --- --- --- --- --- --- --- --- --- --- --- ---
 Q   N   S   S   V   R   G   R   G   I   T   R   L   L   E   S   I   S 1305          1314          1323          1332          1341          1350
AAT TCT TCC AGC AAT ATC CAC AAA TTC TCC AAC TGT GAC ACT TCA CTC TCA CCT
--- --- --- --- --- --- --- --- --- --- --- --- --- --- --- --- --- ---
 N   S   S   S   N   I   H   K   F   S   N   C   D   T   S   L   S   P 1359          1368          1377          1386          1395          1404
TAC ATG TCC CAA AAA GAT GGA TAC AAA TCT TTC TCT TCC TTA TCT TAA TGA TGG
--- --- --- --- --- --- --- --- --- --- --- --- --- --- --- --- --- ---
 Y   M   S   Q   K   D   G   Y   K   S   F   S   S   L   S   *   *

1413          1422          1431          1440          1449          1458
TAC TCT TTT CAA TTT CTG AAA ACA GTA ACA GGC CCA ACT TCC TTC TTA CTA CAG
--- --- --- --- --- --- --- --- --- --- --- --- --- --- --- --- --- ---
        1467          1476          1485          1494          1503          1512
TCA TAT TAA ACA GAT CAC ATC AAT GAC AAA TGT CAC TAC TAT AAA AAC TAC TTA
--- --- --- --- --- --- --- --- --- --- --- --- --- --- --- --- --- ---
        1521          1530          1539          1548          1557          1566
ATT TGT AAG GAA ATT GTT TCA TAG ATT TAA AAA AAT TGT GGT TGG AGA GCA TCT
--- --- --- --- --- --- --- --- --- --- --- --- --- --- --- --- --- ---
        1575          1584          1593          1602          1611          1620
TGG CAT TTG TGC TTT TTT TCT TGA GGG ATT GTT CTG CTT CCT GGC TGT ATG ATG
--- --- --- --- --- --- --- --- --- --- --- --- --- --- --- --- --- ---
```

FIG. 3B

```
              1629          1638          1647          1656          1665          1674
GGT ATA TCA TTA AAG TTT GGA GTC CTA TAT GAA CAA AAC TGA CAT TTT TAG AGT
--- --- --- --- --- --- --- --- --- --- --- --- --- --- --- --- --- ---
              1683          1692          1701          1710          1719          1728
TGT ACT TTT GGG AAT GTT ATA GAT TGA TCA TTC TTT CTC CTG ATA ATA AAG GTA
--- --- --- --- --- --- --- --- --- --- --- --- --- --- --- --- --- ---
         1737          1746          1755
TTG AAT ATC TGT TAA AAA AAA AAA AAA AAA AA 3'
--- --- --- --- --- --- --- --- --- --- --
```

FIG. 3C

```
GATCTTGCCTGATTTCTGATGCCTTTGCCATATGCTTCAAACACCAGTTGACTCTGGTTCTATCATCAGACTTGCA
GTAGATAGGTGGTCAGTTCCCTGGGTTGGGATGAATAAATCTATAAAGGTTTTGTAACACAGTTGCTTGGTTATGC
CCACGTTCAAAATTTGAAATAGGAATCTTGTGACTAGAATCACTTGCAGCCTGACAATGAAATCGAAATCCTCGTG
GAATTTCACCAGGATTTATAAAACTGTGGAAATCTGCCATAATACCTTCTTGGAGAGAATACTTAACACAGCCAAT
TTCACAAGGGAGGAAGCGCTGTTCACAATGAGGAGGTAGCTCGCCATGGCTAAAAATGTTCAAAAAATAAAAAATG
CCTCCAAGGAGAGCTTTTAAAGACAAAGCTGACATATCTGGAGGTGAAACATTCTGCTTTGGTACAAGCATGCCTG
GCCTCCTCAG
```

FIG. 4

```
            1   15 16                30 31                45 46                60 61                75 76                90
1 PTAN-1     MPNRKASRNAYYFFV QEKIPELRRRGLPVA RVADAIPYCSSDWAL LREEEKEKYAEMARE WRAAQGKDPGPSEKQ KPVFTPLRRPGMLVP      90
2 PTAN-2     MPNRKASRNAYYFFV QEKIPELRRRGLPVA RVADAIPYCSSDWA- --------------- --------------- KPVFTPLRRPGMLVP      59
3 PTAN-3     --------------- --------------- --------------- --------------- MARE WRAAQGKDPGPSEKQ KPVFTPLRRPGMLVP   34

91  105 106              120 121               135 136              150 151              165 166              180
1 PTAN-1     KQNVSPPDMSALSLK GDQALLGGIFYFLNI FSHGELPPHCEQRFL PCEIGCVKYSLQEGI MADFHSFINPGEIPR GFRFHCQAASDSSHK      180
2 PTAN-2     KQNVSPPDMSALSLK GDQALLGGIFYFLNI FSHGELPPHCEQRFL PCEIGCVKYSLQEGI MADFHSFINPGEIPR GFRFHCQAASDSSHK      149
3 PTAN-3     KQNVSPPDMSALSLK ---ALLGGIFYFLNI FSHGELPPHCEQRFL PCEIGCVKYSLQEGI MADFHSFINPGEIPR GFRFHCQAASDSSHK      121

181 195 196              210 211               225 226              240 241              255 256              270
1 PTAN-1     IPISNFERGHNQATV LQNLYRFIHPNPGNW PPIYCKSDDRTRVNW CLKHMAKASEIRQDL QLLTVEDLVVGIYQQ KFLKEPSKTWIRSLL      270
2 PTAN-2     IPISNFERGHNQATV LQNLYRFIHPNPGNW PPIYCKSDDRTRVNW CLKHMAKASEIRQDL QLLTVEDLVVGIYQQ KFLKEPSKTWIRSLL      239
3 PTAN-3     IPISNFERGHNQATV LQNLYRFIHPNPGNW PPIYCKSDDRTRVNW CLKHMAKASEIRQDL QLLTVEDLVVGIYQQ KFLKEPSKTWIRSLL      211

271 285 286              300 301               315 316              330 331              345 346              360
1 PTAN-1     DVAMWDYSSNTRCKW HEENDILFCALAVCK KIAYCISNSLATLFG IQLTEAHVPLQDYEA SNSVTPKMVLDAGR YQKLRVGSSGFSHFN       360
2 PTAN-2     DVAMWDYSSNTRCKW HEENDILFCALAVCK KIAYCISNSLATLFG IQLTEAHVPLQDYEA SNSVTPKMVLDAGR YQKLRVGSSGFSHFN       329
3 PTAN-3     DVAMWDYSSNTRCKW HEENDILFCALAVCK KIAYCISNSLATLFG IQLTEAHVPLQDYEA SNSVTPKMVLDAGR YQKLRVGSSGFSIIFN      301

361 375 376              390 391               405 406              420 421              435 436              450
1 PTAN-1     SSNEEQRSNTPIGDY PSRAKISGQNSSVRG RGITRLLESISNSSS NIHKFSNCDTSLSPY MSQKDGYKSFSSLS                           434
2 PTAN-2     SSNEEQRSNTPIGDY PSRAKISGQNSSVRG RGITRLLESISNSSS NIHKFSNCDTSLSPY MSQKDGYKSFSSLS                           403
3 PTAN-3     SSNEEQRSNTPIGDY PSRAKISGQNSSVRG RGITRLLESISNSSS NIHKFSNCDTSLSPY MSQKDGYKSFSSLS                           375
```

FIG. 5

```
              1          15 16            30 31              45 46           60 61            75 76           90
1 PTAN-1    ----------- ------------- ---------------- -----------GGCCA GGA--AGTTTGACCG CGCTGC----- CATGC CGAACCCGTAAGCCCA    44
2 PTAN-2    -----GCCCGGCGAG GGCGCCCGGTGCTTTG TTCTGTCTGAGGCCA GGA--AGTTTGACCG CGCTGC-----CATGC CGAACCCGTAAGGCCA   79
3 PTAN-3    GCGCGGCACGGGGCG AGCGTCTCCCCGCCG CAGAGCCCGCCGCGC GGGGGAGCTCGGCC- CGCCGCACCGCCTCC CGGCGCC-TCCCCCCC   88

91         105 106           120 121          135 136          150 151          165 166          180
1 PTAN-1    GCCG-------- ------GAATGCTTACTATTT CTT-------CGTGC-- ---------------- -AGGAGAAGATCCCC GAACTACGGCGACGA   100
2 PTAN-2    GCCG-------- ------GAATGCTTACTATTT CTT-------CGTGC-- ---------------- -AGGAGAAGATCCCC GAACTACGGCGACGA   135
3 PTAN-3    GCCGCCCGCTGCCGC GACTGCCAAAG-TTT CTCGGTCACGTGCTG GCCCCCGGCGGGCCCA AAGGAGAAGATCCCC GAACTACGGCGACGA   177

181        195 196           210 211          225 226          240 241          255 256          270
1 PTAN-1    GGCCTGCCTGTGGCT CGCGTTGCTGATGCC ATCCCTTACTGCTCC TCAGACTGGGCGCTT CTGAGGGAGGAAGAA AAGGAGAAATACGCA   190
2 PTAN-2    GGCCTGCCTGTGGCT CGCGTTGCTGATGCC ATCCCTTACTGCTCC TCAGACTGGGCGCG-- ---------------- ----------------   192
3 PTAN-3    GGCCTGCCTGTGGCT CGCGTTGCTGATGCC ATCCCTTACTGCTCC TCAGACTGGGCGCTT CTGAGGGAGGAAGAA AAGGAGAAATACGCA   267

271        285 286           300 301          315 316          330 331          345 346          360
1 PTAN-1    GAAATGGCTCGAGAA TGGAGGGCCGCTCAG GGAAAGGACCCCTGGG CCCTCAGAGAAGCAG AAACCTGTTTTCACA CCACTGAGGAGGCCA   280
2 PTAN-2    --------------- --------------- ---------------- --------------- AAACCTGTTTTCACA CCACTGAGGAGGCCA   222
3 PTAN-3    GAAATGGCTCGAGAA TGGAGGGCCGCTCAG GGAAAGGACCCCTGGG CCCTCAGAGAAGCAG AAACCTGTTTTCACA CCACTGAGGAGGCCA   357
```

FIG. 7A

```
              361       375 376       390 391       405 406       420 421       435 436       450
1 PTAN-1      GGCATGCTTGTACCA AAGCAGAATGTTTCA CCTCCAGATATGTCA GCTTTGTCTTTAAAA GGTGATCAAGCTCTC CTTGGAGGCATTTTT    370
2 PTAN-2      GGCATGCTTGTACCA AAGCAGAATGTTTCA CCTCCAGATATGTCA GCTTTGTCTTTAAAA GGTGATCAAGCTCTC CTTGGAGGCATTTTT    312
3 PTAN-3      GGCATGCTTGTACCA AAGCAGAATGTTTCA CCTCCAGATATGTCA GCTTTGTCTTTAAAA G-------CTCTC CTTGGAGGCATTTTT    438

451       465 466       480 481       495 496       510 511       525 526       540
1 PTAN-1      TATTTTTTGAACATT TTTAGCCATGGCGAG CTACCTCCTCCATTGT GAACAGCGCTTCCTC CCTTGTGAAATTGGC TGTGTTAAGTATTCT    460
2 PTAN-2      TATTTTTTGAACATT TTTAGCCATGGCGAG CTACCTCCTCCATTGT GAACAGCGCTTCCTC CCTTGTGAAATTGGC TGTGTTAAGTATTCT    402
3 PTAN-3      TATTTTTTGAACATT TTTAGCCATGGCGAG CTACCTCCTCCATTGT GAACAGCGCTTCCTC CCTTGTGAAATTGGC TGTGTTAAGTATTCT    528

541       555 556       570 571       585 586       600 601       615 616       630
1 PTAN-1      CTCCAAGAAGGTATT ATGGCAGATTTCCAC AGTTTTATAAATCCT GGTGAAATTCCACGA GGATTTCGATTTCAT TGTCAGGCTGCAAGT    550
2 PTAN-2      CTCCAAGAAGGTATT ATGGCAGATTTCCAC AGTTTTATAAATCCT GGTGAAATTCCACGA GGATTTCGATTTCAT TGTCAGGCTGCAAGT    492
3 PTAN-3      CTCCAAGAAGGTATT ATGGCAGATTTCCAC AGTTTTATAAATCCT GGTGAAATTCCACGA GGATTTCGATTTCAT TGTCAGGCTGCAAGT    618

631       645 646       660 661       675 676       690 691       705 706       720
1 PTAN-1      GATTCTAGTCACAAG ATTCCTATTTCAAAT TTTGAACGTGGGCAT AACCAAGCAACTGTG TTACAAAACCTTTAT AGATTATTCATCCC    640
2 PTAN-2      GATTCTAGTCACAAG ATTCCTATTTCAAAT TTTGAACGTGGGCAT AACCAAGCAACTGTG TTACAAAACCTTTAT AGATTATTCATCCC    582
3 PTAN-3      GATTCTAGTCACAAG ATTCCTATTTCAAAT TTTGAACGTGGGCAT AACCAAGCAACTGTG TTACAAAACCTTTAT AGATTATTCATCCC    708

721       735 736       750 751       765 766       780 781       795 796       810
1 PTAN-1      AACCCAGGGAACTGG CCACCTATCTACTGC AAGTCTGATGATAGA ACCAGAGTCAACTGG TGTTTGAAGCATATG GCAAAGGCATCAGAA    730
2 PTAN-2      AACCCAGGGAACTGG CCACCTATCTACTGC AAGTCTGATGATAGA ACCAGAGTCAACTGG TGTTTGAAGCATATG GCAAAGGCATCAGAA    672
3 PTAN-3      AACCCAGGGAACTGG CCACCTATCTACTGC AAGTCTGATGATAGA ACCAGAGTCAACTGG TGTTTGAAGCATATG GCAAAGGCATCAGAA    798

811       825 826       840 841       855 856       870 871       885 886       900
1 PTAN-1      ATCAGGCAAGATCTA CAACTTCTCACTGTA GAGGACCTTGTAGTG GGGATCTACCAACAA AAATTTCTCAAGGAG CCCTCTAAGACTTGG    820
2 PTAN-2      ATCAGGCAAGATCTA CAACTTCTCACTGTA GAGGACCTTGTAGTG GGGATCTACCAACAA AAATTTCTCAAGGAG CCCTCTAAGACTTGG    762
3 PTAN-3      ATCAGGCAAGATCTA CAACTTCTCACTGTA GAGGACCTTGTAGTG GGGATCTACCAACAA AAATTTCTCAAGGAG CCCTCTAAGACTTGG    888
```

FIG. 7B

```
         1261       1275 1276            1290 1291            1305 1306            1320 1321            1335 1336            1350
1 PTAN-1 AGCAGCGTTCGGGGA AGAGGAATTACCCGC TTACTAGAGAGCATT TCCAATTCTTCCAGC AATATCCACAAATTC TCCAACTGTGACACT  1270
2 PTAN-2 AGCAGCGTTCGGGGA AGAGGAATTACCCGC TTACTAGAGAGCATT TCCAATTCTTCCAGC AATATCCACAAATTC TCCAACTGTGACACT  1212
3 PTAN-3 AGCAGCGTTCGGGGA AGAGGAATTACCCGC TTACTAGAGAGCATT TCCAATTCTTCCAGC AATATCCACAAATTC TCCAACTGTGACACT  1338
```

FIG. 7C

```
              1351       1365 1366        1380 1381       1395 1396       1410 1411       1425 1426       1440
1 PTAN-1  TCACTCTCACCTTAC ATGTCCCAAAAAGAT GGATACAAATCTTTC TCTTCCTTATCTTAA TGATGGTACTCTTTT CAATTTCTGAAAACA  1360
2 PTAN-2  TCACTCTCACCTTAC ATGTCCCAAAAAGAT GGATACAAATCTTTC TCTTCCTTATCTTAA TGATGGTACTCTTTT CAATTTCTGAAAACA  1302
3 PTAN-3  TCACTCTCACCTTAC ATGTCCCAAAAAGAT GGATACAAATCTTTC TCTTCCTTATCTTAA TGATGGTACTCTTTT CAATTTCTGAAAACA  1428

1441       1455 1456        1470 1471       1485 1486       1500 1501       1515 1516       1530
1 PTAN-1  GTAACAGGCCCAACT TCCTTCTTACTACAG TCATATTAAACAGAT CACATCAATGACAAA TGTCACTACTATAAA AACTACTTAATTTGT  1450
2 PTAN-2  GTAACAGGCCCAACT TCCTTCTTACTACAG TCATATTAAACAGAT CACATCAATGACAAA TGTCACTACTATAAA AACTACTTAATTTGT  1392
3 PTAN-3  GTAACAGGCCCAACT TCCTTCTTACTACAG TCATATTAAACAGAT CACATCAATGACAAA TGTCACTACTATAAA AACTACTTAATTTGT  1518

1531       1545 1546        1560 1561       1575 1576       1590 1591       1605 1606       1620
1 PTAN-1  AAGGAAATTGTTTCA TAGATTTAAAAAAAT TGTGGTTGGAGAGCA TCTTGGCATTTGTGC TTTTTTTCTTGAGGG ATTGTTCTGCTTCCT  1540
2 PTAN-2  AAGGAAATTGTTTCA TAGATTTAAAAAAAT TGTGGTTGGAGAGCA TCTTGGCATTTGTGC TTTTTTTCTTGAGGG ATTGTTCTGCTTCCT  1482
3 PTAN-3  AAGGAAATTGTTTCA TAGATTTAAAAAAAT TGTGGTTGGAGAGCA TCTTGGCATTTGTGC TTTTTTTCTTGAGGG ATTGTTCTGCTTCCT  1608

1621       1635 1636        1650 1651       1665 1666       1680 1681       1695 1696       1710
1 PTAN-1  GGCTGTATGATGGGT ATATCATTAAAGTTT GGAGTCCTATATGAA CAAAACTGACATTTT TAGAGTTGTACTTTT GGGAATGTTATAGAT  1630
2 PTAN-2  GGCTGTATGATGGGT ATATCATTAAAGTTT GGAGTCCTATATGAA CAAAACTGACATTTT TAGAGTTGTACTTTT GGGAATGTTATAGAT  1572
3 PTAN-3  GGCTGTATGATGGGT ATATCATTAAAGTTT GGAGTCCTATATGAA CAAAACTGACATTTT TAGAGTTGTACTTTT GGGAATGTTATAGAT  1698

1711       1725 1726        1740 1741       1755 1756       1770 1771       1785 1786       1800
1 PTAN-1  TGATCATTCTTTCTC CTGATAATAATAAGTA TTGAATATCTGTTA- -AAA----AAAAAAA AAAAAA--                        1785
2 PTAN-2  TGATCATTCTTTCTC CTGATAATAATAAGTA TTGAATATCTGTTAT GAAAGGTTAAAAAAA AAAAAAAA                        1690
3 PTAN-3  TGATCATTCTTTCTC CTGATAATAATAAGTA TTGAATATCTGTTA- -AAA----AAAAAAA AAAAAAAA                        1760
```

FIG. 7D

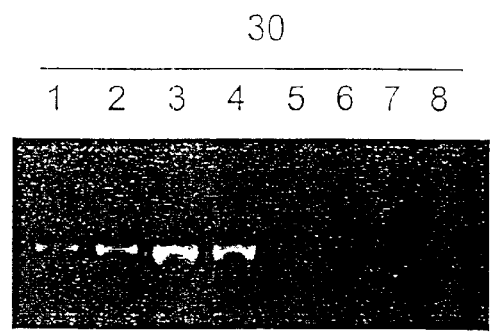
FIG. 8A
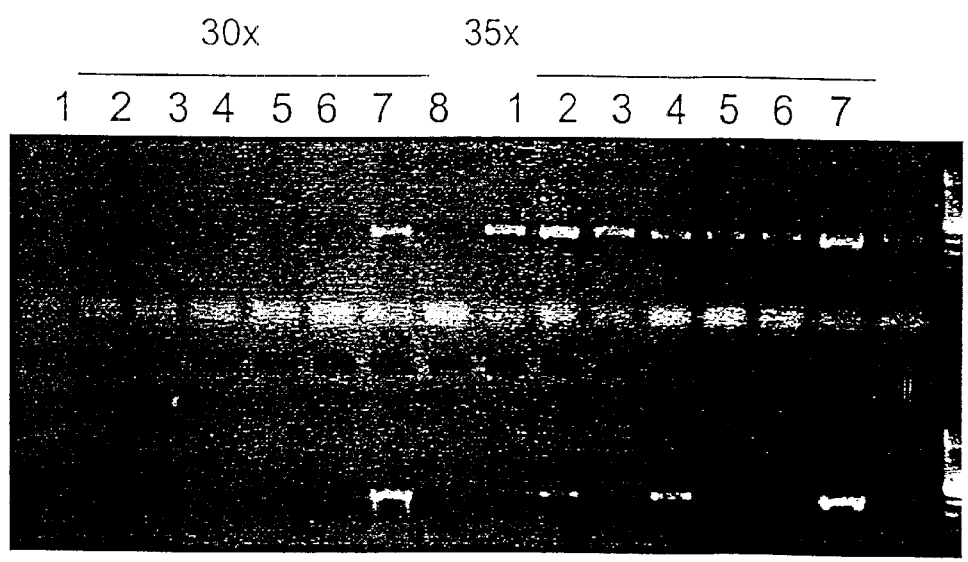
FIG. 8B                    FIG. 8C
Panels:
A
1. Brain
2. Prostate
3. LAPC-4 AD
4. LAPC-4 AI
5. LAPC-9 AD
6. HeLa
7. Murine cDNA
8. Neg. control
B
1. Brain
2. Heart
3. Kidney
4. Liver
5. Lung
6. Pancreas
7. Placenta
8. Skeletal Muscle
C
1. Colon
2. Ovary
3. Leukocytes
4. Prostate
5. Small Intestine
6. Spleen
7. Testis
8. Thymus

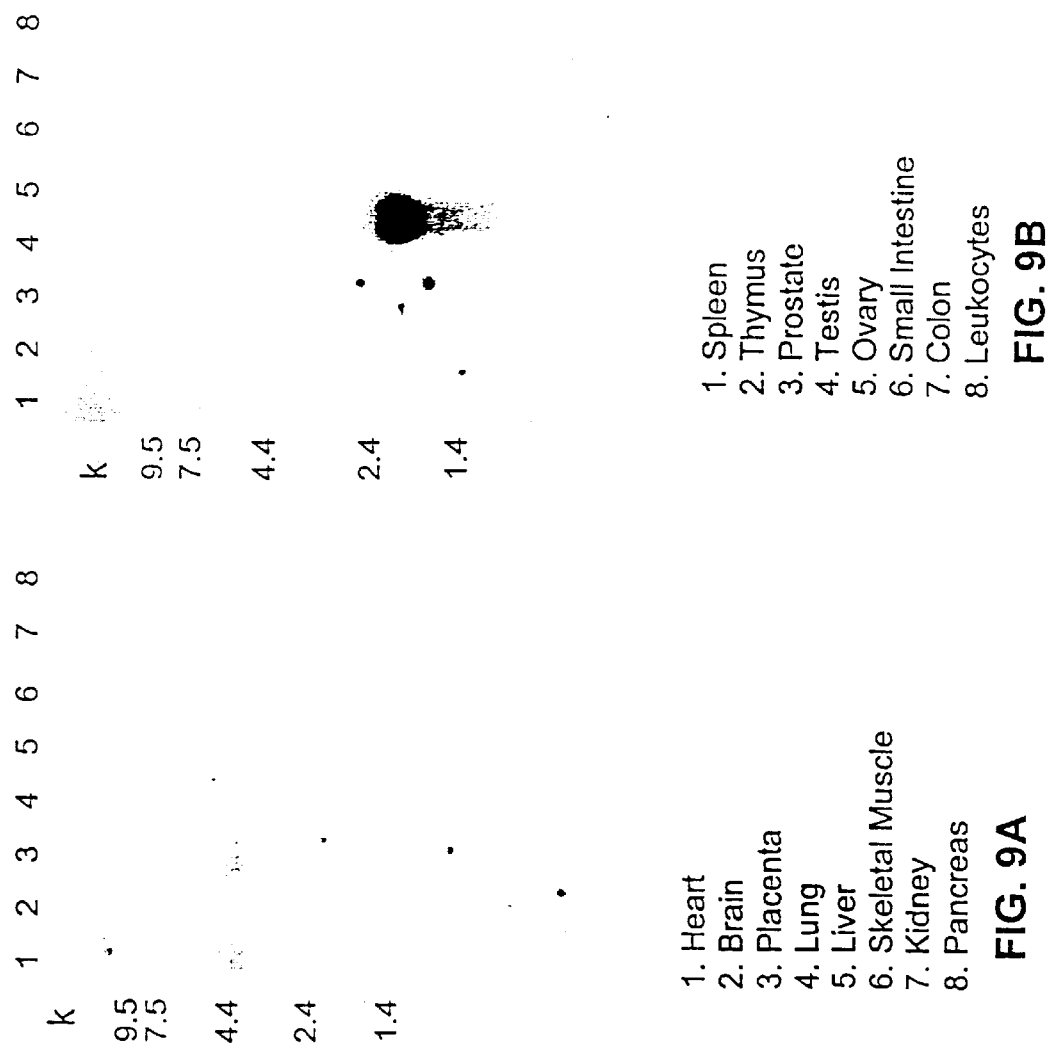

| | 1 | 2 | 3 | 4 | 5 | 6 | 7 | 8 | 9 | 10 | 11 |
|---|---|---|---|---|---|---|---|---|---|---|---|
| A | | | | | | | | | | | |
| B | | | | | | | | | | | |
| C | | | | | | | | | | | |
| D | | | | | | | | | | | |
| E | | | | | | | | | | | |
| F | | | | | | | | | | | |
| G | | | | | | | | | | | |
| H | | | | | | | | | | | |

A1 whole brain
A2 cerebellum, left
A3 substantia nigra
A4 heart
A5 esophagus
A6 colon, transverse
A7 kidney
A8 lung
A9 liver
A10 HL60, leukemia
A11 fetal brain B1 cerebral cortex
B2 cerebellum, right
B3 accumbens nucleus
B4 aorta
B5 stomach
B6 colon, descending
B7 skeletal muscle
B8 placenta
B9 pancreas
B10 HeLa, S3
B11 fetal heart C1 frontal lobe
C2 corpus callosum
C3 thalamus
C4 atrium, left
C5 duodenum
C6 rectum
C7 spleen
C8 bladder
C9 adrenal gland
C10 K562, leukemia
C11 fetal kidney D1 parietal lobe
D2 amygdala
D3 pituitary gland
D4 atrium, right
D5 jejunum
D6 -
D7 thymus
D8 uterus
D9 thyroid gland
D10 MOLT-4, leukemia
D11 fetal liver E1 occipital lobe
E2 caudate nucleus
E3 spinal cord
E4 ventricle, left
E5 ileum
E6 -
E7 leukocytes
E8 prostate
E9 salivary gland
E10 RAJI, lymphoma
E11 fetal spleen F1 temporal lobe
F2 hippocampus
F3 -
F4 ventricle, right
F5 ilocecum
F6 -
F7 lymph node
F8 testis
F9 mammary gland
F10 DAUDI, lymphoma
F11 fetal thymus G1 paracentral gyrus
G2 medulla oblongata
G3 -
G4 interventricular septum
G5 appendix
G6 -
G7 bone marrow
G8 ovary
G9 -
G10 SW480, colon cancer
G11 fetal lung H1 pons
H2 putamen
H3 -
H4 apex of the heart
H5 colon, ascending
H6 -
H7 trachea
H8 -
H9 -
H10 A549, lung cancer
H11 -

FIG. 10

SEQUENCE LISTING

```
<160> NUMBER OF SEQ ID NOS:  23

<210> SEQ ID NO 1
<211> LENGTH: 1690
<212> TYPE: DNA
<213> ORGANISM: Homo sapiens

<400> SEQUENCE: 1
ggccaggaag tttgaccgcg ctgccatgcc gaaccgtaag gccagccgga atgcttacta     60
tttcttcgtg caggagaaga tccccgaact acggcgacga ggcctgcctg tggctcgcgt    120
tgctgatgcc atcccttact gctcctcaga ctgggcgctt ctgagggagg aagaaaagga    180
gaaatacgca gaaatggctc gagaatggag ggccgctcag ggaaaggacc ctgggccctc    240
agagaagcag aaacctgttt tcacaccact gaggaggcca ggcatgcttg taccaaagca    300
gaatgtttca cctccagata tgtcagcttt gtctttaaaa ggtgatcaag ctctccttgg    360
aggcattttt tattttttga acatttttag ccatggcgag ctacctcctc attgtgaaca    420
gcgcttcctc ccttgtgaaa ttggctgtgt taagtattct ctccaagaag gtattatggc    480
agatttccac agtttttataa atcctggtga aattccacga ggatttcgat ttcattgtca    540
ggctgcaagt gattctagtc acaagattcc tatttcaaat tttgaacgtg ggcataacca    600
agcaactgtg ttacaaaacc tttatagatt tattcatccc aacccaggga actggccacc    660
tatctactgc aagtctgatg atagaaccag agtcaactgg tgtttgaagc atatggcaaa    720
ggcatcagaa atcaggcaag atctacaact tctcactgta gaggaccttg tagtggggat    780
ctaccaacaa aaatttctca aggagccctc taagacttgg attcgaagcc tcctagatgt    840
ggccatgtgg gattattcta gcaacacaag gtgcaagtgg catgaagaaa atgatattct    900
cttctgtgct ttagctgttt gcaagaagat tgcgtactgc atcagtaatt ctctggccac    960
tctctttgga atccagctca cagaggctca tgtaccacta caagattatg aggccagcaa   1020
tagtgtgaca cccaaaatgg ttgtattgga tgcagggcgt taccagaagc taagggttgg   1080
gagttcagga ttctctcatt tcaactcttc taatgaggaa caaagatcaa acacacccat   1140
tggtgactac ccatctaggg caaaaatttc tggccaaaac agcagcgttc ggggaagagg   1200
aattacccgc ttactagaga gcatttccaa ttcttccagc aatatccaca aattctcaa    1260 ctgtgacact tcactctcac cttacatgtc ccaaaaagat ggatacaaat ctttctcttc   1320
```

-continued

```
cttatcttaa tgatggtact cttttcaatt tctgaaaaca gtaacaggcc caacttcctt     1380
cttactacag tcatattaaa cagatcacat caatgacaaa tgtcactact ataaaaacta     1440
cttaatttgt aaggaaattg tttcatagat ttaaaaaaat tgtggttgga gagcatcttg     1500
gcatttgtgc ttttttcctt gagggattgt tctgcttcct ggctgtatga tgggtatatc     1560
attaaagttt ggagtcctat atgaacaaaa ctgacatttt tagagttgta cttttgggaa     1620
tgttatagat tgatcattct ttctcctgat aataaggta ttgaatatct gttaaaaaaa      1680
aaaaaaaaaa                                                           1690
```

<210> SEQ ID NO 2
<211> LENGTH: 434
<212> TYPE: PRT
<213> ORGANISM: Homo sapiens

<400> SEQUENCE: 2

```
Met Pro Asn Arg Lys Ala Ser Arg Asn Ala Tyr Tyr Phe Phe Val Gln
 1               5                  10                  15

Glu Lys Ile Pro Glu Leu Arg Arg Arg Gly Leu Pro Val Ala Arg Val
                20                  25                  30

Ala Asp Ala Ile Pro Tyr Cys Ser Ser Asp Trp Ala Leu Leu Arg Glu
            35                  40                  45

Glu Glu Lys Glu Lys Tyr Ala Glu Met Ala Arg Glu Trp Arg Ala Ala
        50                  55                  60

Gln Gly Lys Asp Pro Gly Pro Ser Glu Lys Gln Lys Pro Val Phe Thr
65                  70                  75                  80

Pro Leu Arg Arg Pro Gly Met Leu Val Pro Lys Gln Asn Val Ser Pro
                85                  90                  95

Pro Asp Met Ser Ala Leu Ser Leu Lys Gly Asp Gln Ala Leu Leu Gly
            100                 105                 110

Gly Ile Phe Tyr Phe Leu Asn Ile Phe Ser His Gly Glu Leu Pro Pro
        115                 120                 125

His Cys Glu Gln Arg Phe Leu Pro Cys Glu Ile Gly Cys Val Lys Tyr
    130                 135                 140

Ser Leu Gln Glu Gly Ile Met Ala Asp Phe His Ser Phe Ile Asn Pro
145                 150                 155                 160

Gly Glu Ile Pro Arg Gly Phe Arg Phe His Cys Gln Ala Ala Ser Asp
                165                 170                 175

Ser Ser His Lys Ile Pro Ile Ser Asn Phe Glu Arg Gly His Asn Gln
            180                 185                 190

Ala Thr Val Leu Gln Asn Leu Tyr Arg Phe Ile His Pro Asn Pro Gly
        195                 200                 205

Asn Trp Pro Pro Ile Tyr Cys Lys Ser Asp Asp Arg Thr Arg Val Asn
    210                 215                 220

Trp Cys Leu Lys His Met Ala Lys Ala Ser Glu Ile Arg Gln Asp Leu
225                 230                 235                 240

Gln Leu Leu Thr Val Glu Asp Leu Val Val Gly Ile Tyr Gln Gln Lys
                245                 250                 255

Phe Leu Lys Glu Pro Ser Lys Thr Trp Ile Arg Ser Leu Leu Asp Val
            260                 265                 270

Ala Met Trp Asp Tyr Ser Ser Asn Thr Arg Cys Lys Trp His Glu Glu
        275                 280                 285

Asn Asp Ile Leu Phe Cys Ala Leu Ala Val Cys Lys Lys Ile Ala Tyr
    290                 295                 300
```

```
Cys Ile Ser Asn Ser Leu Ala Thr Leu Phe Gly Ile Gln Leu Thr Glu
305                 310                 315                 320

Ala His Val Pro Leu Gln Asp Tyr Glu Ala Ser Asn Ser Val Thr Pro
                325                 330                 335

Lys Met Val Val Leu Asp Ala Gly Arg Tyr Gln Lys Leu Arg Val Gly
                340                 345                 350

Ser Ser Gly Phe Ser His Phe Asn Ser Ser Asn Glu Glu Gln Arg Ser
            355                 360                 365

Asn Thr Pro Ile Gly Asp Tyr Pro Ser Arg Ala Lys Ile Ser Gly Gln
            370                 375                 380

Asn Ser Ser Val Arg Gly Arg Gly Ile Thr Arg Leu Leu Glu Ser Ile
385                 390                 395                 400

Ser Asn Ser Ser Ser Asn Ile His Lys Phe Ser Asn Cys Asp Thr Ser
                405                 410                 415

Leu Ser Pro Tyr Met Ser Gln Lys Asp Gly Tyr Lys Ser Phe Ser Ser
                420                 425                 430

Leu Ser
```

<210> SEQ ID NO 3
<211> LENGTH: 1640
<212> TYPE: DNA
<213> ORGANISM: Homo sapiens

<400> SEQUENCE: 3

| | | | | | |
|---|---|---|---|---|---|
| gcccggcgag | ggcgccggtg | ctttgttctg | tctgaggcca | ggaagtttga | ccgcgctgcc | 60 |
| atgccgaacc | gtaaggccag | ccggaatgct | tactatttct | tcgtgcagga | gaagatcccc | 120 |
| gaactacggc | gacgaggcct | gcctgtggct | cgcgttgctg | atgccatccc | ttactgctcc | 180 |
| tcagactggg | cgaaacctgt | tttcacacca | ctgaggaggc | caggcatgct | tgtaccaaag | 240 |
| cagaatgttt | cacctccaga | tatgtcagct | tgtctttaa | aaggtgatca | agctctcctt | 300 |
| ggaggcattt | tttatttttt | gaacattttt | agccatggcg | agctacctcc | tcattgtgaa | 360 |
| cagcgcttcc | tccttgtga | aattggctgt | gttaagtatt | ctctccaaga | aggtattatg | 420 |
| gcagatttcc | acagttttat | aaatcctggt | gaaattccac | gaggatttcg | atttcattgt | 480 |
| caggctgcaa | gtgattctag | tcacaagatt | cctatttcaa | attttgaacg | tgggcataac | 540 |
| caagcaactg | tgttacaaaa | cctttataga | tttattcatc | ccaacccagg | gaactggcca | 600 |
| cctatctact | gcaagtctga | tgatagaacc | agagtcaact | ggtgtttgaa | gcatatggca | 660 |
| aaggcatcag | aaatcaggca | agatctacaa | cttctcactg | tagaggacct | tgtagtgggg | 720 |
| atctaccaac | aaaaatttct | caaggagccc | tctaagactt | ggattcgaag | cctcctagat | 780 |
| gtggccatgt | gggattattc | tagcaacaca | aggtgcaagt | ggcatgaaga | aaatgatatt | 840 |
| ctcttctgtg | ctttagctgt | ttgcaagaag | attgcgtact | gcatcagtaa | ttctctggcc | 900 |
| actctctttg | gaatccagct | cacagaggct | catgtaccac | tacaagatta | tgaggccagc | 960 |
| aatagtgtga | cacccaaaat | ggttgtattg | gatgcagggc | gttaccagaa | gctaagggtt | 1020 |
| gggagttcag | gattctctca | tttcaactct | tctaatgagg | aacaaagatc | aaacacaccc | 1080 |
| attggtgact | acccatctag | ggcaaaaatt | tctggccaaa | acagcagcgt | tcggggaaga | 1140 |
| ggaattaccc | gcttactaga | gagcatttcc | aattcttcca | gcaatatcca | caattctcc | 1200 |
| aactgtgaca | cttcactctc | accttacatg | tcccaaaaag | atggatacaa | atctttctct | 1260 |
| tccttatctt | aatgatggta | ctcttttcaa | tttctgaaaa | cagtaacagg | cccaacttcc | 1320 |
| ttcttactac | agtcatatta | aacagatcac | atcaatgaca | aatgtcacta | ctataaaaac | 1380 |

```
tacttaattt gtaaggaaat tgtttcatag attttaaaaa attgtggttg gagagcatct   1440
tggcatttgt gcttttttc ttgagggatt gttctgcttc ctggctgtat gatgggtata    1500
tcattaaagt ttggagtcct atatgaacaa aactgacatt tttagagttg tacttttggg   1560
aatgttatag attgatcatt ctttctcctg ataataaagg tattgaatat ctgttatgaa   1620
aggttaaaaa aaaaaaaaaa                                                1640
```

<210> SEQ ID NO 4
<211> LENGTH: 403
<212> TYPE: PRT
<213> ORGANISM: Homo sapiens

<400> SEQUENCE: 4

```
Met Pro Asn Arg Lys Ala Ser Arg Asn Ala Tyr Tyr Phe Phe Val Gln
 1               5                  10                  15

Glu Lys Ile Pro Glu Leu Arg Arg Arg Gly Leu Pro Val Ala Arg Val
             20                  25                  30

Ala Asp Ala Ile Pro Tyr Cys Ser Ser Asp Trp Ala Lys Pro Val Phe
         35                  40                  45

Thr Pro Leu Arg Arg Pro Gly Met Leu Val Pro Lys Gln Asn Val Ser
     50                  55                  60

Pro Pro Asp Met Ser Ala Leu Ser Leu Lys Gly Asp Gln Ala Leu Leu
 65                  70                  75                  80

Gly Gly Ile Phe Tyr Phe Leu Asn Ile Phe Ser His Gly Glu Leu Pro
                 85                  90                  95

Pro His Cys Glu Gln Arg Phe Leu Pro Cys Glu Ile Gly Cys Val Lys
            100                 105                 110

Tyr Ser Leu Gln Glu Gly Ile Met Ala Asp Phe His Ser Phe Ile Asn
        115                 120                 125

Pro Gly Glu Ile Pro Arg Gly Phe Arg Phe His Cys Gln Ala Ala Ser
    130                 135                 140

Asp Ser Ser His Lys Ile Pro Ile Ser Asn Phe Glu Arg Gly His Asn
145                 150                 155                 160

Gln Ala Thr Val Leu Gln Asn Leu Tyr Arg Phe Ile His Pro Asn Pro
                165                 170                 175

Gly Asn Trp Pro Pro Ile Tyr Cys Lys Ser Asp Asp Arg Thr Arg Val
            180                 185                 190

Asn Trp Cys Leu Lys His Met Ala Lys Ala Ser Glu Ile Arg Gln Asp
        195                 200                 205

Leu Gln Leu Leu Thr Val Glu Asp Leu Val Val Gly Ile Tyr Gln Gln
    210                 215                 220

Lys Phe Leu Lys Glu Pro Ser Lys Thr Trp Ile Arg Ser Leu Leu Asp
225                 230                 235                 240

Val Ala Met Trp Asp Tyr Ser Ser Asn Thr Arg Cys Lys Trp His Glu
                245                 250                 255

Glu Asn Asp Ile Leu Phe Cys Ala Leu Ala Val Cys Lys Lys Ile Ala
            260                 265                 270

Tyr Cys Ile Ser Asn Ser Leu Ala Thr Leu Phe Gly Ile Gln Leu Thr
        275                 280                 285

Glu Ala His Val Pro Leu Gln Asp Tyr Glu Ala Ser Asn Ser Val Thr
    290                 295                 300

Pro Lys Met Val Val Leu Asp Ala Gly Arg Tyr Gln Lys Leu Arg Val
305                 310                 315                 320
```

-continued

```
Gly Ser Ser Gly Phe Ser His Phe Asn Ser Asn Glu Glu Gln Arg
            325                 330                 335

Ser Asn Thr Pro Ile Gly Asp Tyr Pro Ser Arg Ala Lys Ile Ser Gly
            340                 345                 350

Gln Asn Ser Ser Val Arg Gly Arg Gly Ile Thr Arg Leu Leu Glu Ser
            355                 360                 365

Ile Ser Asn Ser Ser Asn Ile His Lys Phe Ser Asn Cys Asp Thr
        370                 375                 380

Ser Leu Ser Pro Tyr Met Ser Gln Lys Asp Gly Tyr Lys Ser Phe Ser
385                 390                 395                 400

Ser Leu Ser

<210> SEQ ID NO 5
<211> LENGTH: 1760
<212> TYPE: DNA
<213> ORGANISM: Homo sapiens

<400> SEQUENCE: 5
```

```
gcgcggcacg gggcgagcgt ctccccgccg cagagcccgc cgcgcggggg agctcggccc      60
gccgcaccgc ctcccgcgcc tccgccccgc cgcccgctgc cgcgactgcc aaagtttctc     120
ggtcacgtgc tggcccccgg cggcccaaag gagaagatcc ccgaactacg gcgacgaggc     180
ctgcctgtgg ctcgcgttgc tgatgccatc ccttactgct cctcagactg gcgcttctg     240
agggaggaag aaaaggagaa atacgcagaa atggctcgag aatggagggc cgctcaggga     300
aaggaccctg ggccctcaga gaagcagaaa cctgttttca caccactgag gaggccaggc     360
atgcttgtac caaagcagaa tgtttcacct ccagatatgt cagctttgtc tttaaaagct     420
ctccttggag gcattttta ttttttgaac attttttagcc atggcgagct acctcctcat     480
tgtgaacagc gcttcctccc ttgtgaaatt ggctgtgtta agtattctct ccaagaaggt     540
attatggcag atttccacag ttttataaat cctggtgaaa ttccacgagg atttcgattt     600
cattgtcagg ctgcaagtga ttctagtcac aagattccta tttcaaattt tgaacgtggg     660
cataaccaag caactgtgtt acaaaacctt tatagattta ttcatcccaa cccagggaac     720
tggccaccta tctactgcaa gtctgatgat agaaccagag tcaactggtg tttgaagcat     780
atggcaaagg catcagaaat caggcaagat ctacaacttc tcactgtaga ggaccttgta     840
gtggggatct accaacaaaa atttctcaag gagccctcta agacttggat tcgaagcctc     900
ctagatgtgg ccatgtggga ttattctagc aacacaaggt gcaagtggca tgaagaaaat     960
gatattctct tctgtgcttt agctgtttgc aagaagattg cgtactgcat cagtaattct    1020
ctggccactc tctttggaat ccagctcaca gaggctcatg taccactaca agattatgag    1080
gccagcaata gtgtgacacc caaaatggtt gtattggatg cagggcgtta ccagaagcta    1140
agggttggga gttcaggatt ctctcatttc aactcttcta atgaggaaca agatcaaac     1200
acacccattg gtgactaccc atctagggca aaatttctg gccaaaacag cagcgttcgg    1260
ggaagaggaa ttacccgctt actagagagc atttccaatt cttccagcaa tatccacaaa    1320
ttctccaact gtgacacttc actctcacct tacatgtccc aaaaagatgg atacaaatct    1380
ttctcttcct tatcttaatg atggtactct tttcaatttc tgaaaacagt aacaggccca    1440
acttccttct tactacagtc atattaaaca gatcacatca atgacaaatg tcactactat    1500
aaaaactact taatttgtaa ggaaattgtt tcatagattt aaaaaaattg tggttggaga    1560
gcatcttggc atttgtgctt ttttcttga gggattgttc tgcttcctgg ctgtatgatg    1620
```

-continued

```
ggtatatcat taaagtttgg agtcctatat gaacaaaact gacattttta gagttgtact    1680
tttgggaatg ttatagattg atcattcttt ctcctgataa taaaggtatt gaatatctgt    1740
taaaaaaaaa aaaaaaaaaa                                                1760
```

<210> SEQ ID NO 6
<211> LENGTH: 375
<212> TYPE: PRT
<213> ORGANISM: Homo sapiens

<400> SEQUENCE: 6

```
Met Ala Arg Glu Trp Arg Ala Ala Gln Gly Lys Asp Pro Gly Pro Ser
 1               5                  10                  15

Glu Lys Gln Lys Pro Val Phe Thr Pro Leu Arg Arg Pro Gly Met Leu
            20                  25                  30

Val Pro Lys Gln Asn Val Ser Pro Pro Asp Met Ser Ala Leu Ser Leu
        35                  40                  45

Lys Ala Leu Leu Gly Gly Ile Phe Tyr Phe Leu Asn Ile Phe Ser His
     50                  55                  60

Gly Glu Leu Pro Pro His Cys Glu Gln Arg Phe Leu Pro Cys Glu Ile
 65                  70                  75                  80

Gly Cys Val Lys Tyr Ser Leu Gln Glu Gly Ile Met Ala Asp Phe His
                85                  90                  95

Ser Phe Ile Asn Pro Gly Glu Ile Pro Arg Gly Phe Arg Phe His Cys
            100                 105                 110

Gln Ala Ala Ser Asp Ser Ser His Lys Ile Pro Ile Ser Asn Phe Glu
        115                 120                 125

Arg Gly His Asn Gln Ala Thr Val Leu Gln Asn Leu Tyr Arg Phe Ile
    130                 135                 140

His Pro Asn Pro Gly Asn Trp Pro Pro Ile Tyr Cys Lys Ser Asp Asp
145                 150                 155                 160

Arg Thr Arg Val Asn Trp Cys Leu Lys His Met Ala Lys Ala Ser Glu
                165                 170                 175

Ile Arg Gln Asp Leu Gln Leu Leu Thr Val Glu Asp Leu Val Val Gly
            180                 185                 190

Ile Tyr Gln Gln Lys Phe Leu Lys Glu Pro Ser Lys Thr Trp Ile Arg
        195                 200                 205

Ser Leu Leu Asp Val Ala Met Trp Asp Tyr Ser Ser Asn Thr Arg Cys
    210                 215                 220

Lys Trp His Glu Glu Asn Asp Ile Leu Phe Cys Ala Leu Ala Val Cys
225                 230                 235                 240

Lys Lys Ile Ala Tyr Cys Ile Ser Asn Ser Leu Ala Thr Leu Phe Gly
                245                 250                 255

Ile Gln Leu Thr Glu Ala His Val Pro Leu Gln Asp Tyr Glu Ala Ser
            260                 265                 270

Asn Ser Val Thr Pro Lys Met Val Leu Asp Ala Gly Arg Tyr Gln
        275                 280                 285

Lys Leu Arg Val Gly Ser Gly Phe Ser His Phe Asn Ser Ser Asn
     290                 295                 300

Glu Glu Gln Arg Ser Asn Thr Pro Ile Gly Asp Tyr Pro Ser Arg Ala
305                 310                 315                 320

Lys Ile Ser Gly Gln Asn Ser Ser Val Arg Gly Arg Gly Ile Thr Arg
                325                 330                 335

Leu Leu Glu Ser Ile Ser Asn Ser Ser Ser Asn Ile His Lys Phe Ser
            340                 345                 350
```

```
Asn Cys Asp Thr Ser Leu Ser Pro Tyr Met Ser Gln Lys Asp Gly Tyr
        355                 360                 365
Lys Ser Phe Ser Ser Leu Ser
    370                 375
```

<210> SEQ ID NO 7
<211> LENGTH: 466
<212> TYPE: DNA
<213> ORGANISM: Homo sapiens

<400> SEQUENCE: 7

```
gatcttgcct gatttctgat gcctttgcca tatgcttcaa acaccagttg actctggttc     60
tatcatcaga cttgcagtag ataggtggtc agttccctgg gttgggatga ataaatctat    120
aaaggttttg taacacagtt gcttggttat gcccacgttc aaaatttgaa ataggaatct    180
tgtgactaga atcacttgca gcctgacaat gaaatcgaaa tcctcgtgga atttcaccag    240
gatttataaa actgtggaaa tctgccataa taccttcttg gagagaatac ttaacacagc    300
caatttcaca agggaggaag cgctgttcac aatgaggagg tagctcgcca tggctaaaaa    360
tgttcaaaaa ataaaaaatg cctccaagga gagcttttaa agacaaagct gacatatctg    420
gaggtgaaac attctgcttt ggtacaagca tgcctggcct cctcag                   466
```

<210> SEQ ID NO 8
<211> LENGTH: 15
<212> TYPE: PRT
<213> ORGANISM: Homo sapiens

<400> SEQUENCE: 8

```
His Ser Ser Lys Glu Lys Leu Arg Arg Glu Arg Ile Lys Tyr Cys
  1               5                  10                  15
```

<210> SEQ ID NO 9
<211> LENGTH: 14
<212> TYPE: DNA
<213> ORGANISM: Artificial Sequence
<220> FEATURE:
<223> OTHER INFORMATION: cDNA Synthesis Primer

<400> SEQUENCE: 9

```
ttttgatcaa gctt                                                      14
```

<210> SEQ ID NO 10
<211> LENGTH: 42
<212> TYPE: DNA
<213> ORGANISM: Artificial Sequence
<220> FEATURE:
<223> OTHER INFORMATION: DNA Adaptor 1

<400> SEQUENCE: 10

```
ctaatacgac tcactatagg gctcgagcgg ccgcccgggc ag                       42
```

<210> SEQ ID NO 11
<211> LENGTH: 12
<212> TYPE: DNA
<213> ORGANISM: Artificial Sequence
<220> FEATURE:
<223> OTHER INFORMATION: DNA Adaptor

<400> SEQUENCE: 11

```
gatcctgccc gg                                                        12
```

```
<210> SEQ ID NO 12
<211> LENGTH: 40
<212> TYPE: DNA
<213> ORGANISM: Artificial Sequence
<220> FEATURE:
<223> OTHER INFORMATION: DNA Adaptor

<400> SEQUENCE: 12
gtaatacgac tcactatagg gcagcgtggt cgcggccgag                            40

<210> SEQ ID NO 13
<211> LENGTH: 10
<212> TYPE: DNA
<213> ORGANISM: Artificial Sequence
<220> FEATURE:
<223> OTHER INFORMATION: DNA Adaptor

<400> SEQUENCE: 13
gatcctcggc                                                            10

<210> SEQ ID NO 14
<211> LENGTH: 22
<212> TYPE: DNA
<213> ORGANISM: Artificial Sequence
<220> FEATURE:
<223> OTHER INFORMATION: PCR Primer 1

<400> SEQUENCE: 14
ctaatacgac tcactatagg gc                                              22

<210> SEQ ID NO 15
<211> LENGTH: 22
<212> TYPE: DNA
<213> ORGANISM: Artificial Sequence
<220> FEATURE:
<223> OTHER INFORMATION: Nested Primer (NP) 1

<400> SEQUENCE: 15
tcgagcggcc gcccgggcag ga                                              22

<210> SEQ ID NO 16
<211> LENGTH: 20
<212> TYPE: DNA
<213> ORGANISM: Artificial Sequence
<220> FEATURE:
<223> OTHER INFORMATION: Nested Primer (NP) 2

<400> SEQUENCE: 16
agcgtggtcg cggccgagga                                                 20

<210> SEQ ID NO 17
<211> LENGTH: 25
<212> TYPE: DNA
<213> ORGANISM: Artificial Sequence
<220> FEATURE:
<223> OTHER INFORMATION: Artificial Primer

<400> SEQUENCE: 17
atatcgccgc gctcgtcgtc gacaa                                           25

<210> SEQ ID NO 18
<211> LENGTH: 25
<212> TYPE: DNA
<213> ORGANISM: Artificial Sequence
<220> FEATURE:
<223> OTHER INFORMATION: Artificial Primer
```

-continued

```
<400> SEQUENCE: 18
agccacacgc agctcattgt agaag                                              25

<210> SEQ ID NO 19
<211> LENGTH: 25
<212> TYPE: DNA
<213> ORGANISM: Artificial Sequence
<220> FEATURE:
<223> OTHER INFORMATION: RT-PCR Primer

<400> SEQUENCE: 19
ttgcagtaga taggtggtca gctcc                                              25

<210> SEQ ID NO 20
<211> LENGTH: 23
<212> TYPE: DNA
<213> ORGANISM: Artificial Sequence
<220> FEATURE:
<223> OTHER INFORMATION: RT-PCR Primer

<400> SEQUENCE: 20
caaagcagaa tgtttcacct cca                                                23

<210> SEQ ID NO 21
<211> LENGTH: 15
<212> TYPE: PRT
<213> ORGANISM: Homo sapiens

<400> SEQUENCE: 21

Cys Gln Ala Ala Ser Asp Ser Ser His Lys Ile Pro Ile Ser Asn
 1               5                  10                  15

<210> SEQ ID NO 22
<211> LENGTH: 24
<212> TYPE: DNA
<213> ORGANISM: Artificial Sequence
<220> FEATURE:
<223> OTHER INFORMATION: PCR Primer

<400> SEQUENCE: 22
tccaattctt ccagcaatat ccac                                               24

<210> SEQ ID NO 23
<211> LENGTH: 24
<212> TYPE: DNA
<213> ORGANISM: Artificial Sequence
<220> FEATURE:
<223> OTHER INFORMATION: PCR Primer

<400> SEQUENCE: 23
aggaagttgg gcctgttact gttt                                               24
```

PTANS: TESTIS SPECIFIC PROTEINS EXPRESSED IN PROSTATE CANCER

CROSS-REFERENCE TO RELATED APPLICATIONS

This Application claims benefit under 35 U.S.C. § 119(e) to provisional applications Ser. No. 60/129,518 filed Apr. 14, 1999; Ser. No. 60/113,229 filed Dec. 21, 1998; Ser. No. 60/102,910 filed Oct. 2, 1998; and Ser. No. 60/102,556 filed Sep. 30, 1998.

FIELD OF THE INVENTION

The invention described herein relates to a novel gene and its encoded proteins, termed PTANs, and to diagnostic and therapeutic methods and compositions useful in the management of various cancers which express PTANs, particularly including prostate and breast cancers.

BACKGROUND OF THE INVENTION

Cancer is the second leading cause of human death next to coronary disease. Worldwide, millions of people die from cancer every year. In the United States alone, cancer causes the death of well over a half-million people annually, with some 1.4 million new cases diagnosed per year. While deaths from heart disease have been declining significantly, those resulting from cancer generally are on the rise. In the early part of the next century, cancer is predicted to become the leading cause of death.

Worldwide, several cancers stand out as the leading killers. In particular, carcinomas of the lung, prostate, breast, colon, pancreas, and ovary represent the primary causes of cancer death. These and virtually all other carcinomas share a common lethal feature. With very few exceptions, metastatic disease from a carcinoma is fatal. Moreover, even for those cancer patients who initially survive their primary cancers, common experience has shown that their lives are dramatically altered. Many cancer patients experience strong anxieties driven by the awareness of the potential for recurrence or treatment failure. Many cancer patients experience physical debilitations following treatment. Many cancer patients experience a recurrence.

Generally speaking, the fundamental problem in the management of the deadliest cancers is the lack of effective and non-toxic systemic therapies. Molecular medicine promises to redefine the ways in which these cancers are managed. Unquestionably, there is an intensive worldwide effort aimed at the development of novel molecular approaches to cancer diagnosis and treatment. For example, there is a great interest in identifying truly tumor-specific genes and proteins that could be used as diagnostic and prognostic markers and/or therapeutic targets or agents. Research efforts in these areas are encouraging, and the increasing availability of useful molecular technologies has accelerated the acquisition of meaningful knowledge about cancer. Nevertheless, progress is slow and generally uneven.

As discussed below, the management of prostate cancer serves as a good example of the limited extent to which molecular biology has translated into real progress in the clinic. With limited exceptions, the situation is more or less the same for the other major carcinomas mentioned above.

Worldwide, prostate cancer is the fourth most prevalent cancer in men. In North America and Northern Europe, it is by far the most common male cancer and is the second leading cause of cancer death in men. In the United States alone, well over 40,000 men die annually of this disease—second only to lung cancer. Despite the magnitude of these figures, there is still no effective treatment for metastatic prostate cancer. Surgical prostatectomy, radiation therapy, hormone ablation therapy, and chemotherapy continue to be the main treatment modalities. Unfortunately, these treatments are ineffective for many and are often associated with undesirable consequences.

On the diagnostic front, the lack of a prostate tumor marker that can accurately detect early-stage, localized tumors remains a significant limitation in the management of this disease. Although the serum PSA assay has been a very useful tool, its specificity and general utility is widely regarded as lacking in several important respects.

Most prostate cancers initially occur in the peripheral zone of the prostate gland, away from the urethra. Tumors within this zone may not produce any symptoms and, as a result, most men with early-stage prostate cancer will not present clinical symptoms of the disease until significant progression has occurred. Tumor progression into the transition zone of the prostate may lead to urethral obstruction, thus producing the first symptoms of the disease. However, these clinical symptoms are indistinguishable from the common non-malignant condition of benign prostatic hyperplasia (BPH). Early detection and diagnosis of prostate cancer currently relies on digital rectal examinations (DRE), prostate specific antigen (PSA) measurements, transrectal ultrasonography (TRUS), and transrectal needle biopsy (TRNB). At present, serum PSA measurement in combination with DRE represent the leading tool used to detect and diagnose prostate cancer. Both have major limitations which have fueled intensive research into finding better diagnostic markers of this disease.

Similarly, there is no available marker that can predict the emergence of the typically fatal metastatic stage of prostate cancer. Diagnosis of metastatic stage is presently achieved by open surgical or laparoscopic pelvic lymphadenectomy, whole body radionuclide scans, skeletal radiography, and/or bone lesion biopsy analysis. Clearly, better imaging and other less invasive diagnostic methods offer the promise of easing the difficulty those procedures place on a patient, as well as improving diagnostic accuracy and opening therapeutic options. A similar problem is the lack of an effective prognostic marker for determining which cancers are indolent and which ones are or will be aggressive. PSA, for example, fails to discriminate accurately between indolent and aggressive cancers. Until there are prostate tumor markers capable of reliably identifying early-stage disease, predicting susceptibility to metastasis, and precisely imaging tumors, the management of prostate cancer will continue to be extremely difficult.

PSA is the most widely used tumor marker for screening, diagnosis, and monitoring prostate cancer today. In particular, several immunoassays for the detection of serum PSA are in widespread clinical use. Recently, a reverse transcriptase-polymerase chain reaction (RT-PCR) assay for PSA mRNA in serum has been developed. However, PSA is not a disease-specific marker, as elevated levels of PSA are detectable in a large percentage of patients with BPH and prostatitis (26–86%)(Gao et al., 1997, Prostate 31: 264–281), as well as in other nonmalignant disorders and in some normal men, a factor which significantly limits the diagnostic specificity of this marker. For example, elevations in serum PSA of between 4 to 10 ng/ml are observed in BPH, and even higher values are observed in prostatitis, particularly acute prostatitis. BPH is an extremely common condition in men. Further confusing the situation is the fact that serum PSA elevations may be observed without any indication of disease from DRE, and visa-versa. Moreover, it is now recognized that PSA is not prostate-specific (Gao et al., supra, for review).

Various methods designed to improve the specificity of PSA-based detection have been described, such as measuring PSA density and the ratio of free vs. complexed PSA. However, none of these methodologies have been able to reproducibly distinguish benign from malignant prostate disease. In addition, PSA diagnostics have sensitivities of between 57–79% (Cupp & Osterling, 1993, Mayo Clin Proc 68:297–306), and thus miss identifying prostate cancer in a significant population of men with the disease.

There are some known markers which are expressed predominantly in prostate, such as prostate specific membrane antigen (PSM), a hydrolase with 85% identity to a rat neuropeptidase (Carter et al., 1996, Proc. Natl. Acad. Sci. USA 93: 749; Bzdega et al., 1997, J. Neurochem. 69: 2270). However, the expression of PSM in small intestine and brain (Israeli et al., 1994, Cancer Res. 54: 1807), as well its potential role in neuropeptide catabolism in brain, raises concern of potential neurotoxicity with anti-PSM therapies. Preliminary results using an Indium-111 labeled, anti-PSM monoclonal antibody to image recurrent prostate cancer show some promise (Sodee et al., 1996, Clin Nuc Med 21: 759–766). More recently identified prostate cancer markers include PCTA-1 (Su et al., 1996, Proc. Natl. Acad. Sci. USA 93: 7252) and prostate stem cell antigen (PSCA) (Reiter et al., 1998, Proc. Natl. Acad. Sci. USA 95: 1735). PCTA-1, a novel galectin, is largely secreted into the media of expressing cells and may hold promise as a diagnostic serum marker for prostate cancer (Su et al., 1996). PSCA, a GPI-linked cell surface molecule, was cloned from LAPC-4 cDNA and is unique in that it is expressed primarily in basal cells of normal prostate tissue and in cancer epithelia (Reiter et al., 1998). Vaccines for prostate cancer are also being actively explored with a variety of antigens, including PSM and PSA.

SUMMARY OF THE INVENTION

The present invention relates to a novel, largely testis-specific gene, designated PTAN, which is over-expressed in prostate cancer. RT-PCR, Northern blot and RNA dot blot expression analysis of PTAN gene expression in normal tissues shows a highly testis-specific expression pattern in adult tissues. Analysis of PTAN expression in normal prostate and prostate tumor xenografts shows over-expression in LAPC4 prostate tumor xenografts. The nucleotide and amino acid sequences of three distinct PTAN isoforms, designated PTAN-1, PTAN-2 and PTAN-3 are shown in FIGS. 1, 2 and 3, respectively (SEQ ID NO:1–6, respectively. The PTANs show significant homology to several testis-derived ESTs but no homology to any known gene in any public database. The testis-specific expression profile of PTAN in normal adult tissues, combined with the over-expression observed in prostate tumor xenografts, suggests that PTAN may be aberrantly over-expressed in at least some prostate cancers, and thus may be a useful diagnostic and/or therapeutic target for prostate cancers.

The invention provides polynucleotides corresponding or complementary to all or part of the PTAN genes, mRNAs, and/or coding sequences, preferably in isolated form, including polynucleotides encoding PTAN proteins and fragments thereof, DNA, RNA, DNA/RNA hybrid, and related molecules, polynucleotides or oligonucleotides complementary to the PTAN genes or mRNA sequences or parts thereof, and polynucleotides or oligonucleotides which hybridize to the PTAN genes, mRNAs, or to PTAN-encoding polynucleotides. Also provided are means for isolating cDNAs and the genes encoding PTAN. Recombinant DNA molecules containing PTAN polynucleotides, cells transformed or transduced with such molecules, and host-vector systems for the expression of PTAN gene products are also provided. The invention further provides PTAN proteins and polypeptide fragments thereof. The invention further provides antibodies that bind to PTAN proteins and polypeptide fragments thereof, including polyclonal and monoclonal antibodies, murine and other mammalian antibodies, chimeric antibodies, humanized and fully human antibodies, antibodies labeled with a detectable marker. The invention further provides methods for detecting the presence of PTAN polynucleotides and proteins in various biological samples, as well as methods for identifying cells that express PTAN. The invention further provides various therapeutic compositions and strategies for treating cancers which express PTAN such as prostate and breast cancers, including therapies aimed at inhibiting the transcription, translation, processing or function of PTAN and cancer vaccines.

BRIEF DESCRIPTION OF THE FIGURES

FIGS. 1(A–B). Nucleotide (SEQ ID NO:1) and amino (SEQ ID NO:2) acid sequences of PTAN-1. See Example 2, infra. D2 clone sequence, putative start methionine with Kozak sequence is indicated in bold, the putative nuclear localization signal is boxed and shaded, a 31 a.a. insert with respect to the C6 sequence (FIG. 2) is indicated in bold and underlined.

FIGS. 2(A–B). Nucleotide (SEQ ID NO:3) and amino acid (SEQ ID NO:4) sequences of PTAN-2. See Example 2, infra. C6 clone sequence, putative start methionine with Kozak sequence is indicated in bold, the putative nuclear localization signal is boxed and shaded.

FIGS. 3(A–B). Nucleotide (SEQ ID NO:5) and amino acid (SEQ ID NO:6) sequences of PTAN-3. See Example 3, infra. C8 clone sequence, putative start methionine with Kozak sequence is indicated in bold, the putative nuclear localization signal is boxed and shaded.

FIG. 4. Nucleotide sequence (SEQ ID NO:7) of SSH-isolated PTAN cDNA fragment clone 26P5C7.

FIG. 5. Amino acid sequence alignment of PTAN-1 (SEQ ID NO:1), PTAN-2 (SEQ ID NO:3) and PTAN-3 (SEQ ID NO:5) isoforms using ClustalW1.7. Amino acid differences are indicated in bold type.

FIGS. 7(A–B). Nucleotide (cDNA) sequence alignment of PTAN-1, PTAN-2 and PTAN-3 isoforms using ClustalW1.7.

FIG. 8. RT-PCR analysis of PTAN gene expression in prostate cancer xenografts, normal prostate, and other tissues and cell lines, showing high level expression in LAPC-4 prostate cancer xenografts and lower level expression in normal prostate (Panel A); and showing detectable expression in normal tissues after 30 cycles of PCR amplification is relatively restricted to testis in normal adult tissues (Panels B and C).

FIGS. 9(A–B). Northern blot analysis of PTAN expression in various normal human tissues showing exclusive expression in testis (using 26P5C7 probe). Size standards in kilobases (kb) are indicated on the side. Each lane contains 2 µg of mRNA. The results show exclusive expression of PTAN in testis.

FIG. 10. An mRNA dot blot analysis of PTAN expression in 76 different samples from human tissues showing exclusive expression in testis (using 26P5C7 probe).

DETAILED DESCRIPTION OF THE INVENTION

Figure 6:
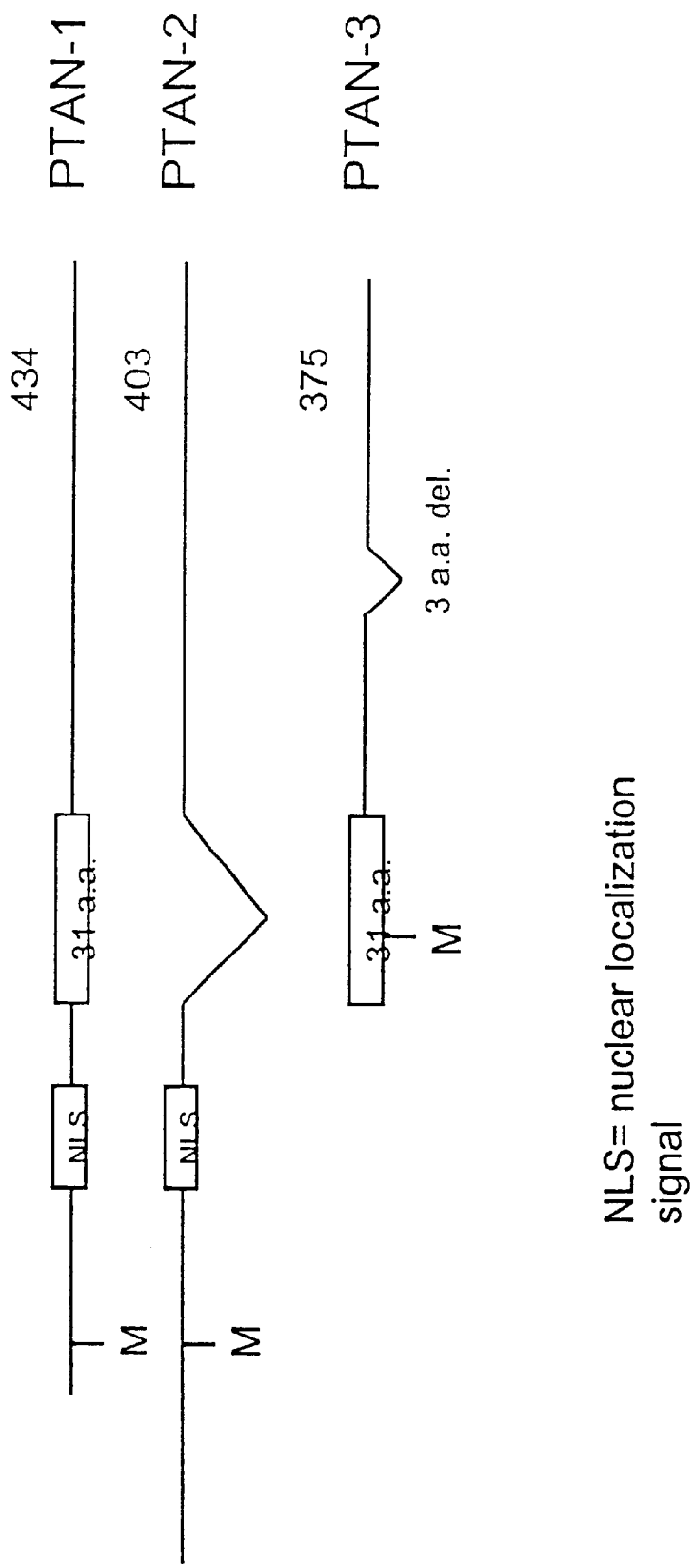
FIG. 6. Schematic representation of the three PTAN isoforms.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the terms "advanced prostate cancer", "locally advanced prostate cancer", "advanced disease" and "locally advanced disease" mean prostate cancers which have extended through the prostate capsule, and are meant to include stage C disease under the American Urological Association (AUA) system, stage C1–C2 disease under the Whitmore-Jewett system, and stage T3–T4 and N+ disease under the TNM (tumor, node, metastasis) system. In general, surgery is not recommended for patients with locally advanced disease, and these patents have substantially less favorable outcomes compared to patients having clinically localized (organ-confined) prostate cancer. Locally advanced disease is clinically identified by palpable evidence of induration beyond the lateral border of the prostate, or asymmetry or induration above the prostate base. Locally advanced prostate cancer is presently diagnosed pathologically following radical prostatectomy if the tumor invades or penetrates the prostate capsule, extends into the surgical margin, or invades the seminal vesicles.

As used herein, the terms "metastatic prostate cancer" and "metastatic disease" mean prostate cancers which have spread to regional lymph nodes or to distant sites, and are meant to include stage D disease under the AUA system and stage TxNxM+ under the TNM system. As is the case with locally advanced prostate cancer, surgery is generally not indicated for patients with metastatic disease, and hormonal (androgen ablation) therapy is the preferred treatment modality. Patients with metastatic prostate cancer eventually develop an androgen-refractory state within 12 to 18 months of treatment initiation, and approximately half of these patients die within 6 months thereafter. The most common site for prostate cancer metastasis is bone. Prostate cancer bone metastases are, on balance, characteristically osteoblastic rather than osteolytic (i.e., resulting in net bone formation). Bone metastases are found most frequently in the spine, followed by the femur, pelvis, rib cage, skull and humerus. Other common sites for metastasis include lymph nodes, lung, liver and brain. Metastatic prostate cancer is typically diagnosed by open or laparoscopic pelvic lymphadenectomy, whole body radionuclide scans, skeletal radiography, and/or bone lesion biopsy.

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA.

As used herein, the term "polypeptide" means a polymer of at least 10 amino acids. Throughout the specification, standard three letter or single letter designations for amino acids are used.

As used herein, the terms "hybridize", "hybridizing", "hybridizes" and the like, used in the context of polynucleotides, are meant to refer to conventional hybridization conditions, preferably such as hybridization in 50% formamide/6×SSC/0.1% SDS/100 μg/ml ssDNA, in which temperatures for hybridization are above 37 degrees C. and temperatures for washing in 0.1×SSC/0.1% SDS are above 55 degrees C., and most preferably to stringent hybridization conditions.

In the context of amino acid sequence comparisons, the term "identity" is used to express the percentage of amino acid residues at the same relative position which are the same. Also in this context, the term "homology" is used to express the percentage of amino acid residues at the same relative positions which are either identical or are similar, using the conserved amino acid criteria of BLAST analysis, as is generally understood in the art. Further details regarding amino acid substitutions, which are considered conservative under such criteria, are provided below.

Additional definitions are provided throughout the subsections which follow.

STRUCTURE AND EXPRESSION OF PTANs

As is further described in the Examples which follow, the PTAN genes and proteins have been characterized using a number of analytical approaches. For example, analyses of nucleotide coding and amino acid sequences were conducted in order to identify potentially related molecules and three distinct PTAN isoforms, as well as recognizable structural domains, topological features, and other elements within the PTAN mRNA and protein structures. RT-PCR, Northern blot and RNA dot blot analyses of PTAN mRNA expression were conducted in order to establish the range of normal and cancerous tissues expressing PTAN message. Western blot analyses were used to characterize anti-PTAN antibody preparations.

A comparative schematic diagram of the three PTAN protein isoform structures is shown in FIG. 6. The nucleotide and amino acid sequences of the full length cDNA clones corresponding to PTAN-1 (1690 bp SEQ ID NO:1,2), PTAN-2 (1640 bp SEQ ID NO:3,4) and PTAN-3 (1760 bp SEQ ID NO:5,6) are shown in FIGS. 1, 2 and 3, respectively. These cDNAs encode open reading frames (ORF) of 434, 403 and 375 amino acids, respectively. Sequence analysis shows no significant homology to any known genes. PTAN-1 and PTAN-2 have a nuclear localization signal (NLS) at the amino-terminus (FIGS. 1, 2). PTAN-1 differs from PTAN-2 by containing a 31 a.a. domain (residues 45–75) that is absent in PTAN-2 (FIG. 1, FIG. 5). PTAN-3 lacks the amino-terminal NLS, exhibits its start methionine within the 31 a.a. domain unique to PTAN-1 and exhibits a 3 amino acid deletion with respect to PTAN-1 and PTAN-2 (residues 106–108 in PTAN-1) (FIG. 5).

The differences between the PTAN isoforms are shown in an alignment in FIG. 5. Differences between the PTAN isoforms are also detected in the 5' untranslated regions (UTRs). The 5'UTRs for PTAN-1 and PTAN-2 are the same, while the 5'UTR for PTAN-3 is significantly different (FIG. 7). In all three PTANs, the 5'UTRs contain sequences rich in GC content (68–70%) indicating that these sequences contain regulatory elements. The PTAN proteins may be factors that potentially regulate transcription.

Recombinant PTAN-1 is expressed as a 49 kD protein in a mammalian expression system. Recombinant PTAN-2 is expressed as a 46 kD protein in the same system. The human PTAN gene maps to chromosome 1 q22.

Figure 11:
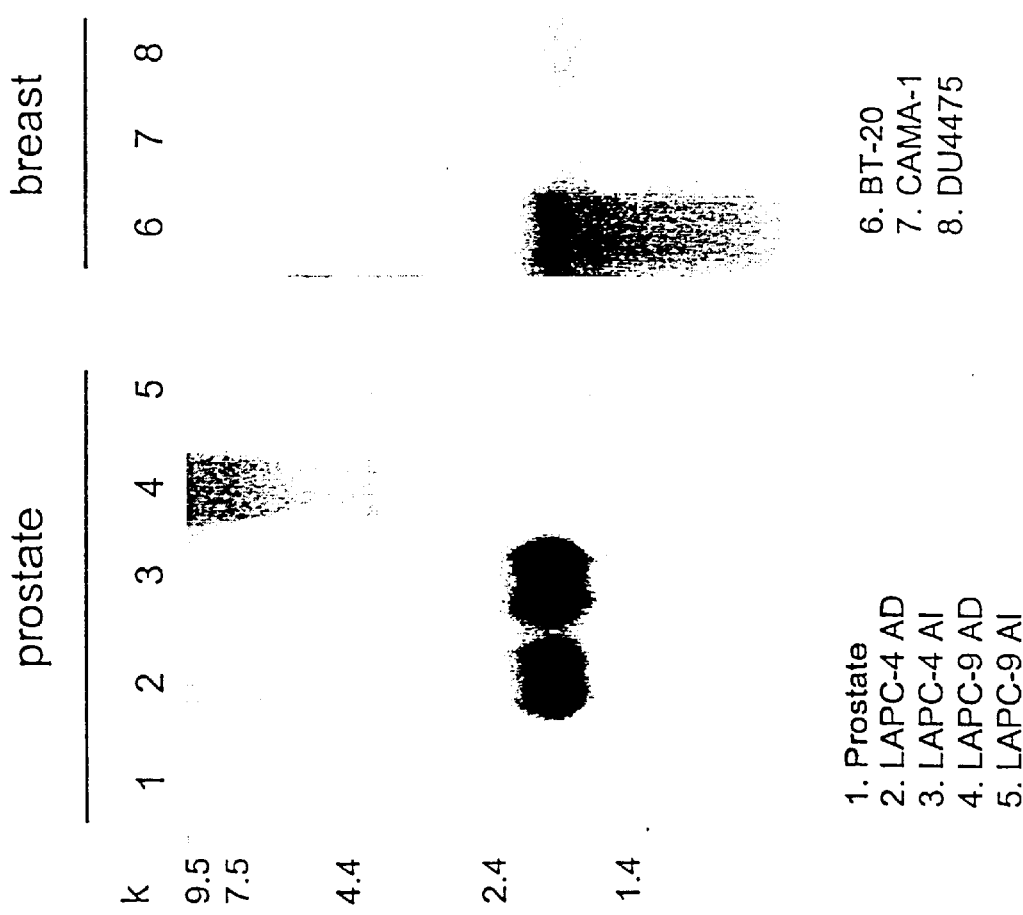
FIG. 11. Northern blot analysis showing PTAN expression in human prostate cancer xenografts and breast cancer cell lines (using 26P5C7 probe). Xenograft and cell line filters were prepared with 10 μg of total RNA per lane. The blots were analyzed using a 26P5C7/PTAN derived gene fragment probe. All RNA samples were normalized by ethidium bromide staining. Kilobases=kb.

PTAN expression is testis-specific in normal adult human tissues (FIGS. 9 and 10), but is also expressed in certain cancers, including prostate and breast cancers. (FIG. 11). Human prostate tumor xenografts originally derived from a patient with high grade metastatic prostate cancer express high levels of PTAN (FIG. 11). Lower level PTAN expression is detected in breast cancer cell lines, suggesting that PTAN is a highly testis-specific gene that may be up-regulated in various human cancers.

PTAN POLYNUCLEOTIDES

One aspect of the invention provides polynucleotides corresponding or complementary to all or part of a PTAN gene, mRNA, and/or coding sequence, preferably in isolated form, including polynucleotides encoding a PTAN protein and fragments thereof, DNA, RNA, DNA/RNA hybrid, and related molecules, polynucleotides or oligonucleotides complementary to a PTAN gene or mRNA sequence or a part thereof, and polynucleotides or oligonucleotides which hybridize to a PTAN gene, mRNA, or to a PTAN-encoding polynucleotide (collectively, "PTAN polynucleotides"). As used herein, the PTAN gene and protein is meant to include the PTAN genes and proteins specifically described herein and the genes and proteins corresponding to other PTAN proteins and structurally similar variants of the foregoing. Such other PTAN proteins and variants will generally have coding sequences which are highly homologous to the PTAN coding sequence, and preferably will share at least about 50% amino acid identity and at least about 60% amino acid homology (using BLAST criteria), more preferably sharing 70% or greater homology (using BLAST criteria).

One embodiment of a PTAN polynucelotide is a PTAN-1 polynucleotide having the sequence shown in FIG. 1 (SEQ ID NO:1). Another embodiment is a PTAN-2 polynucleotide having the nucleotide sequence shown in FIG. 2 (SEQ ID NO:3). Another embodiment is a PTAN-2 polynucleotide having the nucleotide sequence shown in FIG. 3 (SEQ ID NO:5).

A PTAN polynucleotide may comprise a polynucleotide having the nucleotide sequence of human PTAN-1 as shown in FIG. 1 (SEQ ID NO:1) wherein T can also be U; a polynucleotide which encodes all or part of the PTAN-1 protein; a sequence complementary to the foregoing; or a polynucleotide fragment of any of the foregoing. Another embodiment comprises a polynucleotide having the sequence as shown in FIG. 1 (SEQ ID NO:1) from nucleotide residue number 26 through nucleotide residue number 1327, wherein T can also be U. Another embodiment comprises a polynucleotide encoding a PTAN-1 polypeptide whose sequence is encoded by the cDNA contained in the plasmid as deposited with American Type Culture Collection as Accession No. 98976. Another embodiment comprises a polynucleotide which is capable of hybridizing under stringent hybridization conditions to the human PTAN-1 cDNA shown in FIG. 1 (SEQ ID NO:1) or to a polynucleotide fragment thereof.

Similarly, a PTAN polynucleotide may comprise a polynucleotide having the nucleotide sequence of human PTAN-2 as shown in FIG. 2 (SEQ ID NO:3) wherein T can also be U; a polynucleotide which encodes all or part of the PTAN-2 protein; a sequence complementary to the foregoing; or a polynucleotide fragment of any of the foregoing. Another embodiment comprises a polynucleotide having the sequence as shown in FIG. 2 (SEQ ID NO:3), from nucleotide residue number 61 through nucleotide residue number 1269, wherein T can also be U. Another embodiment comprises a polynucleotide encoding a PTAN-2 polypeptide whose sequence is encoded by the cDNA contained in the plasmid as deposited with American Type Culture Collection as Accession No. 98977. Another embodiment comprises a polynucleotide which is capable of hybridizing under stringent hybridization conditions to the human PTAN-2 cDNA shown in FIG. 2 (SEQ ID NO:3) or to a polynucleotide fragment thereof.

Further, a PTAN polynucleotide may comprise a polynucleotide having the nucleotide sequence of human PTAN-3 as shown in FIG. 3 (SEQ ID NO:5), wherein T can also be U; a polynucleotide which encodes all or part of the PTAN-3 protein; a sequence complementary to the foregoing; or a polynucleotide fragment of any of the foregoing. Another embodiment comprises a polynucleotide having the sequence as shown in FIG. 3 (SEQ ID NO:5), from nucleotide residue number 271 through nucleotide residue number 1395, wherein T can also be U. Another embodiment comprises a polynucleotide encoding a PTAN-3 polypeptide whose sequence is encoded by the cDNA contained in the plasmid as deposited with American Type Culture Collection as Accession No. 207095. Another embodiment comprises a polynucleotide which is capable of hybridizing under stringent hybridization conditions to the human PTAN-3 cDNA shown in FIG. 3 (SEQ ID NO:5) or to a polynucleotide fragment thereof.

Specifically contemplated are genomic DNA, cDNAs, ribozymes, and antisense molecules, as well as nucleic acid molecules based on an alternative backbone or including alternative bases, whether derived from natural sources or synthesized. For example, antisense molecules can be RNAs or other molecules, including peptide nucleic acids (PNAs) or non-nucleic acid molecules such as phosphorothioate derivatives, that specifically bind DNA or RNA in a base pair-dependent manner. A skilled artisan can readily obtain these classes of nucleic acid molecules using the PTAN polynucleotides and polynucleotide sequences disclosed herein.

Further specific embodiments of this aspect of the invention include primers and primer pairs, which allow the specific amplification of the polynucleotides of the invention or of any specific parts thereof, and probes that selectively or specifically hybridize to nucleic acid molecules of the invention or to any part thereof. Probes may be labeled with a detectable marker, such as, for example, a radioisotope, fluorescent compound, bioluminescent compound, a chemiluminescent compound, metal chelator or enzyme. Such probes and primers can be used to detect the presence of a PTAN polynucleotide in a sample and as a means for detecting a cell expressing a PTAN protein. Examples of such probes include polynucleotide comprising all or part of the human PTAN cDNA sequences shown in FIGS. 1, 2 and 3 (SEQ ID NO:1,3 and 5, respectively). Examples of primer pairs capable of specifically amplifying PTAN mRNAs are also described in the Examples which follow. As will be understood by the skilled artisan, a great many different primers and probes may be prepared based on the sequences provided in herein and used effectively to amplify and/or detect a PTAN mRNA.

As used herein, a polynucleotide is said to be "isolated" when it is substantially separated from contaminant polynucleotides which correspond or are complementary to genes other than the PTAN gene or which encode polypeptides other than PTAN gene product or fragments thereof. A skilled artisan can readily employ nucleic acid isolation procedures to obtain an isolated PTAN polynucleotide.

The PTAN polynucleotides of the invention are useful for a variety of purposes, including but not limited to their use as probes and primers for the amplification and/or detection of the PTAN gene(s), mRNA(s), or fragments thereof; as reagents for the diagnosis and/or prognosis of prostate cancer and other cancers; as coding sequences capable of directing the expression of PTAN polypeptides; as tools for modulating or inhibiting the expression of the PTAN gene(s) and/or translation of the PTAN transcript(s); and as therapeutic agents.

METHODS FOR ISOLATING PTAN-ENCODING NUCLEIC ACID MOLECULES

The PTAN cDNA sequences described herein enable the isolation of other polynucleotides encoding. PTAN gene product(s), as well as the isolation of polynucleotides encoding PTAN gene product homologues, alternatively spliced isoforms, allelic variants, and mutant forms of the PTAN gene product. Various molecular cloning methods that can be employed to isolate full length cDNAs encoding a PTAN gene are well known (See, for example, Sambrook, J. et al., Molecular Cloning: A Laboratory Manual, 2d edition., Cold Spring Harbor Press, New York, 1989; Current Protocols in Molecular Biology. Ausubel et al., Eds., Wiley and Sons, 1995). For example, lambda phage cloning methodologies may be conveniently employed, using commercially available cloning systems (e.g., Lambda ZAP Express, Stratagene). Phage clones containing PTAN gene cDNAs may be identified by probing with a labeled PTAN cDNA or a fragment thereof. For example, in one embodiment, the PTAN cDNA (FIGS. 1, 2, 3(SEQ ID NO:1,3 and 5, respectively) or a portion thereof can be synthesized and used as a probe to retrieve overlapping and full length cDNAs corresponding to a PTAN gene. The PTAN gene itself may be isolated by screening genomic DNA libraries, bacterial artificial chromosome libraries (BACs), yeast artificial chromosome libraries (YACs), and the like, with PTAN DNA probes or primers.

RECOMBINANT DNA MOLECULES AND HOST-VECTOR SYSTEMS

The invention also provides recombinant DNA or RNA molecules containing a PTAN polynucleotide, including but not limited to phages, plasmids, phagemids, cosmids, YACs, BACs, as well as various viral and non-viral vectors well known in the art, and cells transformed or transfected with such recombinant DNA or RNA molecules. As used herein, a recombinant DNA or RNA molecule is a DNA or RNA molecule that has been subjected to molecular manipulation in vitro. Methods for generating such molecules are well known (see, for example, Sambrook et al, 1989, supra).

The invention further provides a host-vector system comprising a recombinant DNA molecule containing a PTAN polynucleotide within a suitable prokaryotic or eukaryotic host cell. Examples of suitable eukaryotic host cells include a yeast cell, a plant cell, or an animal cell, such as a mammalian cell or an insect cell (e.g., a baculovirus-infectible cell such as an Sf9 or HighFive cell). Examples of suitable mammalian cells include various prostate cancer cell lines such LnCaP, PC-3, DU145, LAPC4, TsuPr1, other transfectable or transducible prostate cancer cell lines, as well as a number of mammalian cells routinely used for the expression of recombinant proteins (e.g., COS, CHO, 293, 293T cells). More particularly, a polynucleotide comprising the coding sequence of a PTAN may be used to generate PTAN proteins or fragments thereof using any number of host-vector systems routinely used and widely known in the art.

A wide range of host-vector systems suitable for the expression of PTAN proteins or fragments thereof are available, see for example, Sambrook et al., 1989, supra; Current Protocols in Molecular Biology, 1995, supra). Preferred vectors for mammalian expression include but are not limited to pcDNA 3.1 myc-His-tag (Invitrogen) and the retroviral vector pSRαtkneo (Muller et al., 1991, MCB .11:1785). Using these expression vectors, PTAN may be preferably expressed in several prostate cancer and non-prostate cell lines, including for example 293, 293T, rat-1, 3T3, PC-3, LNCaP and TsuPr1. The host-vector systems of the invention are useful for the production of a PTAN protein or fragment thereof. Such host-vector systems may be employed to study the functional properties of PTAN and PTAN mutations.

Recombinant human PTAN protein may be produced by mammalian cells transfected with a construct encoding PTAN. In a particular embodiment described in the Examples, 293T cells are transfected with an expression plasmid encoding PTAN, the PTAN protein is expressed in the 293T cells, and the recombinant PTAN protein is isolated using standard purification methods (e.g., affinity purification using anti-PTAN antibodies). In another embodiment, also described in the Examples herein, the PTAN coding sequence is subcloned into the retroviral vector pSRαMSVtkneo and used to infect various mammalian cell lines, including 3T3CL7, PC3 and LnCaP in order to establish PTAN expressing cell lines. Various other expression systems well known in the art may also be employed. Expression constructs encoding a leader peptide joined in frame to the PTAN coding sequence may be used for the generation of a secreted form of recombinant PTAN protein.

Proteins encoded by the PTAN genes, or by fragments thereof, will have a variety of uses, including but not limited to generating antibodies and in methods for identifying ligands and other agents (i.e., other bHLH proteins) and cellular constituents that bind to a PTAN gene product. Antibodies raised against a PTAN protein or fragment thereof may be useful in diagnostic and prognostic assays, and imaging methodologies in the management of human cancers characterized by expression of PTAN protein, including but not limited to cancers of the prostate and breast. Such antibodies may be expressed intracellularly and used in methods of treating patients with such cancers. Various immunological assays useful for the detection of PTAN proteins are contemplated, including but not limited to various types of radioimmunoassays, enzyme-linked immunosorbent assays (ELISA), enzyme-linked immunofluorescent assays (ELIFA), immunocytochemical methods, and the like. Such antibodies may be labeled and used as immunological imaging reagents capable of detecting PTAN expressing cells (e.g., in radioscintigraphic imaging methods). PTAN proteins may also be particularly useful in generating cancer vaccines, as further described below.

PTAN PROTEINS

Another aspect of the present invention provides PTAN proteins and polypeptide fragments thereof. The PTAN proteins of the invention include those specifically identified herein, as well as allelic variants, conservative substitution variants and homologs that can be isolated/generated and characterized without undue experimentation following the methods outlined below. Fusion proteins which combine parts of different PTAN proteins or fragments thereof, as well as fusion proteins of a PTAN protein and a heterologous polypeptide are also included. Such PTAN proteins will be collectively referred to as the PTAN proteins, the proteins of the invention, or PTAN. As used herein, the term "PTAN polypeptide" refers to a polypeptide fragment or a PTAN protein of at least 10 amino acids, preferably at least 15 amino acids.

Specific embodiments of PTAN proteins comprises a polypeptide having the amino acid sequence of human PTAN1, -2, and -3 as shown in FIGS. 1, 2 and 3 (SEQ ID NO:2, 4 and 6, respective), respectively.

In general, naturally occurring allelic variants of human PTAN will share a high degree of structural identity and homology (e.g., 90% or more identity). Typically, allelic variants of the PTAN proteins will contain conservative amino acid substitutions within the PTAN sequences described herein or will contain a substitution of an amino acid from a corresponding position in a PTAN homologue. One class of PTAN allelic variants will be proteins that share a high degree of homology with at least a small region of a particular PTAN amino acid sequence, but will further contain a radical departure form the sequence, such as a non-conservative substitution, truncation, insertion or frame shift.

Conservative amino acid substitutions can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

PTAN proteins may be embodied in many forms, preferably in isolated form. As used herein, a protein is said to be "isolated" when physical, mechanical or chemical methods are employed to remove the PTAN protein from cellular constituents that are normally associated with the protein. A skilled artisan can readily employ standard purification methods to obtain an isolated PTAN protein. A purified PTAN protein molecule will be substantially free of other proteins or molecules which impair the binding of PTAN to antibody or other ligand. The nature and degree of isolation and purification will depend on the intended use. Embodiments of a PTAN protein include a purified PTAN protein and a functional, soluble PTAN protein. In one form, such functional, soluble PTAN proteins or fragments thereof retain the ability to bind antibody or other ligand.

The invention also provides PTAN polypeptides comprising biologically active fragments of the PTAN amino acid sequence, such as a polypeptide corresponding to part of the amino acid sequences for PTAN as shown in FIGS. 1, 2 and 3 (SEQ ID NO:2, 4 and 6, respective). Such polypeptides of the invention exhibit properties of the PTAN protein, such as the ability to elicit the generation of antibodies which specifically bind an epitope associated with the PTAN protein.

PTAN polypeptides can be generated using standard peptide synthesis technology or using chemical cleavage methods well known in the art based on the amino acid sequences of the human PTAN proteins disclosed herein. Alternatively, recombinant methods can be used to generate nucleic acid molecules that encode a polypeptide fragment of a PTAN protein. In this regard, the PTAN-encoding nucleic acid molecules described herein provide means for generating defined fragments of PTAN proteins. PTAN polypeptides are particularly useful in generating and characterizing domain specific antibodies (e.g., antibodies recognizing an extracellular or intracellular epitope of a PTAN protein), in identifying agents or cellular factors that bind to PTAN or a particular structural domain thereof, and in various therapeutic contexts, including but not limited to cancer vaccines.

Polypeptides comprising amino acid sequences which are unique to a particular PTAN protein (relative to other PTAN proteins) may be used to generate antibodies which will specifically react with that particular PTAN protein. For example, referring to the amino acid alignment of the PTANs shown in FIG. 5, the skilled artisan will, readily appreciate that each molecule contains stretches of sequence unique to its structure. These unique stretches can be used to generate PTAN-1, PTAN-2 or PTAN-3 specific antibodies.

PTAN polypeptides containing particularly interesting structures can be predicted and/or identified using various analytical techniques well known in the art, including, for example, the methods of Chou-Fasman, Garnier-Robson, Kyte-Doolittle, Eisenberg, Karplus-Schultz or Jameson-Wolf analysis, or on the basis of immunogenicity. Fragments containing such structures are particularly useful in generating subunit specific anti-PTAN antibodies or in identifying cellular factors that bind to PTAN.

In a specific embodiment described in the examples which follow, PTAN is conveniently expressed in 293T cells transfected with a CMV-driven expression vector encoding PTAN with a C-terminal 6xHis and MYC tag (pcDNA3.1/mycHIS, Invitrogen). The secreted HIS-tagged PTAN in the culture media may be purified using a nickel column using standard techniques.

PTAN ANTIBODIES

Another aspect of the invention provides antibodies that bind to PTAN proteins and polypeptides. The most preferred antibodies will specifically bind to a PTAN protein and will not bind (or will bind weakly) to non-PTAN proteins and polypeptides. Anti-PTAN antibodies that are particularly contemplated include monoclonal and polyclonal antibodies as well as fragments containing the antigen binding domain and/or one or more complementarity determining regions of these antibodies. As used herein, an antibody fragment is defined as at least a portion of the variable region of the immunoglobulin molecule which binds to its target, i.e., the antigen binding region.

PTAN antibodies of the invention may be particularly useful in prostate cancer diagnostic and prognostic assays, and imaging methodologies. Intracellularly expressed antibodies (e.g., single chain antibodies) may be therapeutically useful in treating cancers in which the expression of PTAN is involved, such as for example advanced and metastatic prostate cancers. Similarly, such antibodies may be useful in the treatment, diagnosis, and/or prognosis of other cancers, to the extent PTAN is also expressed or overexpressed in other types of cancer. Other cancers that expresses PTAN include without limitation breast cancer.

The invention also provides various immunological assays useful for the detection and quantification of PTAN and mutant PTAN proteins and polypeptides. Such assays generally comprise one or more PTAN antibodies capable of recognizing and binding a PTAN or mutant PTAN protein, as appropriate, and may be performed within various immunological assay formats well known in the art, including but not limited to various types of radioimmunoassays, enzyme-linked immunosorbent assays (ELISA), enzyme-linked immunofluorescent assays (ELIFA), and the like. In addition, immunological imaging methods capable of detecting prostate cancer and other cancers expressing PTAN (e.g., breast cancer) are also provided by the invention, including but limited to radioscintigraphic imaging methods using labeled PTAN antibodies. Such assays may be clinically useful in the detection, monitoring, and prognosis of PTAN expressing cancers such as prostate cancer.

PTAN antibodies may also be used in methods for purifying PTAN and mutant PTAN proteins and polypeptides and for isolating PTAN homologues and related molecules. For example, in one embodiment, the method of purifying a PTAN protein comprises incubating a PTAN antibody, which has been coupled to a solid matrix, with a lysate or other solution containing PTAN under conditions which permit the PTAN antibody to bind to PTAN; washing the solid matrix to eliminate impurities; and eluting the PTAN from the coupled antibody. Other uses of the PTAN antibodies of the invention include generating anti-idiotypic antibodies that mimic the PTAN protein.

Various methods for the preparation of antibodies are well known in the art. For example, antibodies may be prepared by immunizing a suitable mammalian host using a PTAN protein, peptide, or fragment, in isolated or immunoconjugated form (Antibodies: A Laboratory Manual, CSH Press, Eds., Harlow, and Lane (1988); Harlow, Antibodies, Cold Spring Harbor Press, NY (1989)). In addition, fusion proteins of PTAN may also be used, such as a PTAN GST-fusion protein. In a particular embodiment, a GST fusion protein comprising all or most of the open reading frame amino acid sequence of FIG. 2 may be produced and used as an immunogen to generate appropriate antibodies. In another embodiment, a PTAN peptide may be synthesized and used as an immunogen. As described in Example 6, below, the 15-mer PTAN peptide CQAASDSSHKIPISN (SEQ. ID. NO: 21) was conjugated to keyhole limpet hemocyanin (KLH) and used to immunize a rabbit. The resulting polyclonal antiserum specifically recognized PTAN expressed in a recombinant mammalian expression system.

In addition, naked DNA immunization techniques known in the art may be used (with or without purified PTAN protein or PTAN expressing cells) to generate an immune response to the encoded immunogen (for review, see Donnelly et al., 1997, Ann. Rev. Immunol. 15: 617–648).

The amino acid sequence of the PTANs as shown in FIGS. 1–3 (SEQ ID NO:2, 4 and 6, respectively) may be used to select specific regions of the PTAN protein for generating antibodies. For example, hydrophobicity and hydrophilicity analyses of the PTAN amino acid sequence may be used to identify hydrophilic regions in the PTAN structure. Regions of the PTAN protein that show immunogenic structure, as well as other regions and domains, can readily be identified using various other methods known in the art, such as Chou-Fasman, Gamier-Robson, Kyte-Doolittle, Eisenberg, Karplus-Schultz or Jameson-Wolf analysis. Methods for the generation of PTAN antibodies are further illustrated by way of the examples provided herein.

Methods for preparing a protein or polypeptide for use as an immunogen and for preparing immunogenic conjugates of a protein with a carrier such as BSA, KLH, or other carrier proteins are well known in the art. In some circumstances, direct conjugation using, for example, carbodiimide reagents may be used; in other instances linking reagents such as those supplied by Pierce Chemical Co., Rockford, Ill., may be effective. Administration of a PTAN immunogen is conducted generally by injection over a suitable time period and with use of a suitable adjuvant, as is generally understood in the art. During the immunization schedule, titers of antibodies can be taken to determine adequacy of antibody formation.

PTAN monoclonal antibodies are preferred and may be produced by various means well known in the art. For example, immortalized cell lines which secrete a desired monoclonal antibody may be prepared using the standard hybridoma technology of Kohler and Milstein or modifications which immortalize producing B cells, as is generally known. The immortalized cell lines secreting the desired antibodies are screened by immunoassay in which the antigen is the PTAN protein or a PTAN fragment. When the appropriate immortalized cell culture secreting the desired antibody is identified, the cells may be expanded and antibodies produced either from in vitro cultures or from ascites fluid.

The antibodies or fragments may also be produced, using current technology, by recombinant means. Regions that bind specifically to the desired regions of the PTAN protein can also be produced in the context of chimeric or CDR grafted antibodies of multiple species origin. Humanized or human PTAN antibodies may also be produced and are preferred for use in therapeutic contexts. Methods for humanizing murine and other non-human antibodies by substituting one or more of the non-human antibody CDRs for corresponding human antibody sequences are well known (see for example, Jones et al., 1986, Nature 321: 522–525; Riechmnan et al., 1988, Nature 332: 323–327; Verhoeyen et al., 1988, Science 239: 1534–1536). See also, Carter et al., 1993, Proc. Natl. Acad. Sci. USA 89: 4285 and Sims et al., 1993, J. Immunol. 151: 2296. Methods for producing fully human monoclonal antibodies include phage display and transgenic methods (for review, see Vaughan et al., 1998, Nature Biotechnology 16: 535–539).

Fully human PTAN monoclonal antibodies may be generated using cloning technologies employing large human Ig gene combinatorial libraries (i.e., phage display) (Griffiths and Hoogenboom, Building an in vitro immune system: human antibodies from phage display libraries. In: Protein Engineering of Antibody Molecules for Prophylactic and Therapeutic Applications in Man. Clark, M. (Ed.), Nottingham Academic, pp 45–64 (1993); Burton and Barbas, Human Antibodies from combinatorial libraries. Id., pp 65–82). Fully human PTAN monoclonal antibodies may also be produced using transgenic mice engineered to contain human immunoglobulin gene loci as described in PCT Patent Application WO98/24893, Kucherlapati and Jakobovits et al., published Dec. 3, 1997 (see also, Jakobovits, 1998, Exp. Opin. Invest. Drugs 7(4): 607–614). This method avoids the in vitro manipulation required with phage display technology and efficiently produces high affinity authentic human antibodies.

Reactivity of PTAN antibodies with a PTAN protein may be established by a number of well known means, including Western blot, immunoprecipitation, ELISA, and FACS analyses using, as appropriate, PTAN proteins, peptides, PTAN-expressing cells or extracts thereof.

A PTAN antibody or fragment thereof of the invention may be labeled with a detectable marker or conjugated to a second molecule. Suitable detectable markers include, but are not limited to, a radioisotope, a fluorescent compound, a bioluminescent compound, chemiluminescent compound, a metal chelator or an enzyme. Further, bi-specific antibodies specific for two or more PTAN epitopes may be generated using methods generally known in the art. Homodimeric antibodies may also be generated by cross-linking techniques known in the art (e.g., Wolff et al., Cancer Res. 53: 2560–2565).

METHODS FOR THE DETECTION OF PTAN

Another aspect of the present invention relates to methods for detecting PTAN polynucleotides and PTAN proteins, as well as methods for identifying a cell which expresses PTAN.

More particularly, the invention provides assays for the detection of PTAN polynucleotides in a biological sample, such as serum, bone, prostate, and other tissues, urine, semen, cell preparations, and the like. Detectable PTAN polynucleotides include, for example, a PTAN gene or fragments thereof, PTAN mRNA, alternative splice variant PTAN mRNAs, and recombinant DNA or RNA molecules containing a PTAN polynucleotide. A number of methods for amplifying and/or detecting the presence of PTAN polynucleotides are well known in the art and may be employed in the practice of this aspect of the invention.

In one embodiment, a method for detecting a PTAN mRNA in a biological sample comprises producing cDNA from the sample by reverse transcription using at least one primer; amplifying the cDNA so produced using a PTAN polynucleotides as sense and antisense primers to amplify PTAN cDNAs therein; and detecting the presence of the amplified PTAN cDNA. In another embodiment, a method of detecting a PTAN gene in a biological sample comprises first isolating genomic DNA from the sample; amplifying the isolated genomic DNA using PTAN polynucleotides as sense and antisense primers to amplify the PTAN gene therein; and detecting the presence of the amplified PTAN gene. Any number of appropriate sense and antisense probe combinations may be designed from the nucleotide sequences provided for the PTANs (FIGS. 1–3 (SEQ ID NO:1, 3 and 5, respectively)) and used for this purpose.

The invention also provides assays for detecting the presence of a PTAN protein in a tissue of other biological sample such as serum, bone, prostate, and other tissues, urine, cell preparations, and the like. Methods for detecting a PTAN protein are also well known and include, for example, immunoprecipitation, immunohistochemical analysis, Western Blot analysis, molecular binding assays, ELISA, ELIFA and the like. For example, in one embodiment, a method of detecting the presence of a PTAN protein in a biological sample comprises first contacting the sample with a PTAN antibody, a PTAN-reactive fragment thereof, or a recombinant protein containing an antigen binding region of a PTAN antibody; and then detecting the binding of PTAN protein in the sample thereto.

Methods for identifying a cell which expresses PTAN are also provided. In one embodiment, an assay for identifying a cell which expresses a PTAN gene comprises detecting the presence of PTAN mRNA in the cell. Methods for the detection of particular mRNAs in cells are well known and include, for example, hybridization assays using complementary DNA probes (such as in situ hybridization using labeled PTAN riboprobes, Northern blot and related techniques) and various nucleic acid amplification assays (such as RT-PCR using complementary primers specific for PTAN, and other amplification type detection methods, such as, for example, branched DNA, SISBA, TMA and the like). Alternatively, an assay for identifying a cell which expresses a PTAN gene comprises detecting the presence of PTAN protein in the cell or secreted by the cell. Various methods for the detection of proteins are well known in the art and may be employed for the detection of PTAN proteins and PTAN expressing cells.

PTAN expression analysis may also be useful as a tool for identifying and evaluating agents which modulate PTAN gene expression. For example, PTAN expression is significantly upregulated in prostate cancer, and may also be expressed in other cancers. Identification of a molecule or biological agent that could inhibit PTAN expression or over-expression in cancer cells may be of therapeutic value. Such an agent may be identified by using a screen that quantifies PTAN expression by RT-PCR, nucleic acid hybridization or antibody binding.

ASSAYS FOR DETERMINING PTAN EXPRESSION STATUS

Determining the status of PTAN expression patterns in an individual may be used to diagnose cancer and may provide prognostic information useful in defining appropriate therapeutic options. Similarly, the expression status of PTAN may provide information useful for predicting susceptibility to particular disease stages, progression, and/or tumor aggressiveness. The invention provides methods and assays for determining PTAN expression status and diagnosing cancers which express PTAN, such as cancers of the prostate and breast. PTAN expression status in patient samples may be analyzed by a number of means well known in the art, including without limitation, immunohistochemical analysis, in situ hybridization, RT-PCR analysis on laser capture micro-dissected samples, western blot analysis of clinical samples and cell lines, and tissue array analysis.

In one aspect, the invention provides assays useful in determining the presence of cancer in an individual, comprising detecting a significant increase in PTAN mRNA or protein expression in a test cell or tissue sample relative to expression levels in the corresponding normal cell or tissue. The presence of PTAN mRNA may, for example, be evaluated in tissue samples including but not limited to colon, lung, prostate, pancreas, bladder, breast, ovary, cervix, testis, head and neck, brain, stomach, etc. The presence of significant PTAN expression in any of these tissues may be useful to indicate the emergence, presence and/or severity of these cancers, since the corresponding normal tissues do not express PTAN mRNA or express it at lower levels.

In a related embodiment, PTAN expression status may be determined at the protein level rather than at the nucleic acid level. For example, such a method or assay would comprise determining the level of PTAN protein expressed by cells in a test tissue sample and comparing the level so determined to the level of PTAN expressed in a corresponding normal sample. In one embodiment, the presence of PTAN protein is evaluated, for example, using immunohistochemical methods. PTAN antibodies or binding partners capable of detecting PTAN protein expression may be used in a variety of assay formats well known in the art for this purpose.

In addition, peripheral blood may be conveniently assayed for the presence of cancer cells, including but not limited to prostate and breast cancers, using RT-PCR to detect PTAN expression. The presence of RT-PCR amplifiable PTAN mRNA provides an indication of the presence of the cancer. RT-PCR detection assays for tumor cells in peripheral blood are currently being evaluated for use in the diagnosis and management of a number of human solid tumors. In the prostate cancer field, these include RT-PCR assays for the detection of cells expressing PSA and PSM (Verkaik et al., 1997, Urol. Res. 25: 373–384; Ghossein et al., 1995, J. Clin. Oncol. 13:1195–2000; Heston et al., 1995, Clin. Chem. 41:1687–1688). RT-PCR assays are well known in the art.

A related aspect of the invention is directed to predicting susceptibility to developing cancer in an individual. In one embodiment, a method for predicting susceptibility to cancer comprises detecting PTAN mRNA or PTAN protein in a tissue sample, its presence indicating susceptibility to cancer, wherein the degree of PTAN mRNA expression present is proportional to the degree of susceptibility. In a specific embodiment, the presence of PTAN in prostate tissue is examined, with the presence of PTAN in the sample providing an indication of prostate cancer susceptibility (or the emergence or existence of a prostate tumor). In another specific embodiment, the presence of PTAN in breast tissue is examined, with the presence of PTAN in the sample providing an indication of breast cancer susceptibility (or the emergence or existence of a breast tumor).

Yet another related aspect of the invention is directed to methods for gauging tumor aggressiveness. In one embodiment, a method for gauging aggressiveness of a tumor comprises determining the level of PTAN mRNA or PTAN protein expressed by cells in a sample of the tumor, comparing the level so determined to the level of PTAN mRNA or PTAN protein expressed in a corresponding normal tissue taken from the same individual or a normal tissue reference sample, wherein the degree of PTAN mRNA or PTAN protein expression in the tumor sample relative to the normal sample indicates the degree of aggressiveness. In a specific embodiment, aggressiveness of prostate or breast tumors is evaluated by determining the extent to which PTAN is expressed in the tumor cells, with higher expression levels indicating more aggressive tumors.

Methods for detecting and quantifying the expression of PTAN mRNA or protein are described herein and use standard nucleic acid and protein detection and quantification technologies well known in the art. Standard methods for the detection and quantification of PTAN mRNA include in situ hybridization using labeled PTAN riboprobes, Northern blot and related techniques using PTAN polynucleotide probes, RT-PCR analysis using primers specific for PTAN, and other amplification type detection methods, such as, for example, branched DNA, SISBA, TMA and the like. In a specific embodiment, semi-quantitative RT-PCR may be used to detect and quantify PTAN mRNA expression as described in the Examples which follow. Any number of primers capable of amplifying PTAN may be used for this purpose, including but not limited to the various primer sets specifically described herein. Standard methods for the detection and quantification of protein may be used for this purpose. In a specific embodiment, polyclonal or monoclonal antibodies specifically reactive with the wild-type PTAN protein may be used in an immunohistochemical assay of biopsied tissue.

THERAPEUTIC METHODS AND COMPOSITIONS

The identification of PTAN as a normally testis-specific protein that is also expressed in cancers of the prostate and breast (and possibly other cancers), opens a number of therapeutic approaches to the treatment of such cancers. As discussed above, it is possible that PTAN functions as a transcription factor involved in activating tumor-promoting genes or repressing genes that block tumorigenesis.

Accordingly, therapeutic approaches aimed at inhibiting the activity of the PTAN protein are expected to be useful for patients suffering from prostate cancer, breast cancer, and other cancers expressing PTAN. These therapeutic approaches generally fall into two classes. One class comprises various methods for inhibiting the binding or association of the PTAN protein with its binding partner or with others proteins. Another class comprises a variety of methods for inhibiting the transcription of the PTAN gene or translation of PTAN mRNA.

A. THERAPEUTIC INHIBITION OF PTAN WITH INTRACELLULAR ANTIBODIES

Recombinant vectors encoding single chain antibodies which specifically bind to PTAN may be introduced into PTAN expressing cells via gene transfer technologies, wherein the encoded single chain anti-PTAN antibody is expressed intracellularly, binds to PTAN protein, and thereby inhibits its function. Methods for engineering such intracellular single chain antibodies are well known. Such intracellular antibodies, also known as "intrabodies", may be specifically targeted to a particular compartment within the cell, providing control over where the inhibitory activity of the treatment will be focused. This technology has been successfully applied in the art (for review, see Richardson and Marasco, 1995, TIBTECH vol. 13). Intrabodies have been shown to virtually eliminate the expression of otherwise abundant cell surface receptors. See, for example, Richardson et al., 1995, Proc. Natl. Acad. Sci. USA 92: 3137–3141; Beerli et al., 1994, J. Biol. Chem. 289: 23931–23936; Deshane et al., 1994, Gene Ther. 1: 332–337.

Single chain antibodies comprise the variable domains of the heavy and light chain joined by a flexible linker polypeptide, and are expressed as a single polypeptide. Optionally, single chain antibodies may be expressed as a single chain variable region fragment joined to the light chain constant region. Well known-intracellular trafficking signals may be engineered into recombinant polynucleotide vectors encoding such single chain antibodies in order to precisely target the expressed intrabody to the desired intracellular compartment. For example, intrabodies targeted to the endoplasmic reticulum (ER) may be engineered to incorporate a leader peptide and, optionally, a C-terminal ER retention signal, such as the KDEL amino acid motif. Intrabodies intended to exert activity in the nucleus may be engineered to include a nuclear localization signal. Lipid moieties may be joined to intrabodies in order to tether the intrabody to the cytosolic side of the plasma membrane. Intrabodies may also be targeted to exert function in the cytosol. For example, cytosolic intrabodies may be used to sequester factors within the cytosol, thereby preventing them from being transported to their natural cellular destination.

In one embodiment, intrabodies may be used to capture PTAN in the nucleus, thereby preventing its activity within the nucleus. Nuclear targeting signals may be engineered into such PTAN intrabodies in order to achieve the desired targeting. Such PTAN intrabodies may be designed to bind specifically to a particular PTAN domain, such as, for example, the bHLH domain of the PTAN protein. In another embodiment, cytosolic intrabodies which specifically bind to the PTAN protein may be used to prevent PTAN from gaining access to the nucleus, thereby preventing it from exerting any biological activity within the nucleus (e.g., preventing PTAN from forming transcription complexes with other factors).

In order to specifically direct the expression of such intrabodies to particular tumor cells, the transcription of the intrabody may be placed under the regulatory control of an appropriate tumor-specific promoter and/or enhancer. In order to target intrabody expression specifically to prostate, for example, the PSA promoter and/or promoter/enhancer may be utilized (See, for example, U.S. Pat. No. 5,919,652).

B. THERAPEUTIC METHODS BASED ON INHIBITION OF PTAN TRANSCRIPTION OR TRANSLATION

Within the second class of therapeutic approaches, the invention provides various methods and compositions for inhibiting the transcription of the PTAN gene. Similarly, the invention also provides methods and compositions for inhibiting the translation of PTAN mRNA into protein.

In one approach, a method of inhibiting the transcription of the PTAN gene comprises contacting the PTAN gene with a PTAN antisense polynucleotide. In another approach, a method of inhibiting PTAN mRNA translation comprises contacting the PTAN mRNA with an antisense polynucleotide. In another approach, a PTAN specific ribozyme may be used to cleave the PTAN message, thereby inhibiting translation. Such antisense and ribozyme based methods may also be directed to the regulatory regions of the PTAN gene, such as the PTAN promoter and/or enhancer elements. Similarly, proteins capable of inhibiting a PTAN gene transcription factor may be used to inhibit PTAN mRNA transcription. The various polynucleotides and compositions useful in the aforementioned methods have been described above. The use of antisense and ribozyme molecules to inhibit transcription and translation is well known in the art.

Other factors which inhibit the transcription of PTAN through interfering with PTAN transcriptional activation may also be useful for the treatment of cancers expressing PTAN. Similarly, factors which are capable of interfering with PTAN processing may be useful for the treatment of cancers expressing PTAN. Cancer treatment methods utilizing such factors are also within the scope of the invention.

C. GENERAL CONSIDERATIONS

Gene transfer and gene therapy technologies may be used for delivering therapeutic polynucleotide molecules to tumor cells synthesizing PTAN (i.e., antisense, ribozyme, polynucleotides encoding intrabodies and other PTAN inhibitory molecules). A number of gene therapy approaches are known in the art Recombinant vectors encoding PTAN antisense polynucleotides, ribozymes, factors capable of interfering with PTAN transcription, and so forth, may be delivered to target tumor cells using such gene therapy approaches.

The above therapeutic approaches may be combined with chemotherapy or radiation therapy regimens. These therapeutic approaches may also enable the use of reduced dosages of chemotherapy and/or less frequent administration, particularly in patients that do not tolerate the toxicity of the chemotherapeutic agent well.

The anti-tumor activity of a particular composition (e.g., antisense, ribozyme, intrabody), or a combination of such compositions, may be evaluated using various in vitro and in vivo assay systems. In vitro assays for evaluating therapeutic potential include cell growth assays, soft agar assays and other assays indicative of tumor promoting activity, binding assays capable of determining the extent to which a therapeutic composition will inhibit the binding of PTAN to a binding partner, etc.

In vivo, the effect of a PTAN therapeutic composition may be evaluated in a suitable animal model. For example, xenogenic prostate cancer models wherein human prostate cancer explants or passaged xenograft tissues are introduced into immune compromised animals, such as nude or SCID mice, are appropriate in relation to prostate cancer and have been described (Klein et al., 1997, Nature Medicine 3: 402–408). For Example, PCT Patent Application WO98/16628, Sawyers et al., published Apr. 23, 1998, describes various xenograft models of human prostate cancer capable of recapitulating the development of primary tumors, micrometastasis, and the formation of osteoblastic metastases characteristic of late stage disease. Efficacy may be predicted using assays which measure inhibition of tumor formation, tumor regression or metastasis, and the like. See, also, the Examples below.

In vivo assays which qualify the promotion of apoptosis may also be useful in evaluating potential therapeutic compositions. In one embodiment, xenografts from bearing mice treated with the therapeutic composition may be examined for the presence of apoptotic foci and compared to untreated control xenograft-bearing mice. The extent to which apoptotic foci are found in the tumors of the treated mice provides an indication of the therapeutic efficacy of the composition.

The therapeutic compositions used in the practice of the foregoing methods may be formulated into pharmaceutical compositions comprising a carrier suitable for the desired delivery method. Suitable carriers include any material which when combined with the therapeutic composition retains the anti-tumor function of the therapeutic composition and is non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Edition, A. Osal., Ed., 1980).

Therapeutic formulations may be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. A preferred formulation for intravenous injection comprises the therapeutic composition in a solution of preserved bacteriostatic water, sterile unpreserved water, and/or diluted in polyvinylchloride or polyethylene bags containing 0.9% sterile Sodium Chloride for Injection, USP. Therapeutic protein preparations may be lyophilized and stored as sterile powders, preferably under vacuum, and then reconstituted in bacteriostatic water containing, for example, benzyl alcohol preservative, or in sterile water prior to injection.

Dosages and administration protocols for the treatment of cancers using the foregoing methods will vary with the method and the target cancer and will generally depend on a number of other factors appreciated in the art.

CANCER VACCINES

The invention further provides prostate cancer vaccines comprising a PTAN protein or fragment thereof, as well as DNA based vaccines. In view of the testis-restricted expression of PTAN in normal human tissues (and the existence of the testis-blood barrier), PTAN cancer vaccines are expected to be effective at specifically preventing and/or treating PTAN expressing cancers without creating non-specific effects on non-target tissues. The use of a tumor antigen in a vaccine for generating humoral and cell-mediated immunity for use in anti-cancer therapy is well known in the art and has been employed in prostate cancer using human PSMA and rodent PAP immunogens (Hodge et al., 1995, Int. J. Cancer 63: 231–237; Fong et al., 1997, J. Immunol. 159: 3113–3117). Such methods can be readily practiced by employing a PTAN protein, or fragment thereof, or a PTAN-encoding nucleic acid molecule and recombinant vectors capable of expressing and appropriately presenting the PTAN immunogen.

For example, viral gene delivery systems may be used to deliver a PTAN-encoding nucleic acid molecule. Various viral gene delivery systems which can be used in the practice of this aspect of the invention include, but are not limited to, vaccinia, fowlpox, canarypox, adenovirus, influenza, poliovirus, adeno-associated virus, lentivirus, and sindbus virus (Restifo, 1996, Curr. Opin. Immunol. 8: 658–663). Non-viral delivery systems may also be employed by using naked DNA encoding a PTAN protein or fragment thereof introduced into the patient (e.g., intramuscularly) to induce an anti-tumor response. In one embodiment, the full-length human PTAN cDNA may be employed. In another embodiment, PTAN nucleic acid molecules encoding specific cytotoxic T lymphocyte (CTL) epitopes may be employed. CTL epitopes can be determined using specific algorithms (e.g., Epimer, Brown University) to identify peptides within a PTAN protein which are capable of optimally binding to specified HLA alleles.

Various ex vivo strategies may also be employed. One approach involves the use of dendritic cells to present .PTAN antigen to a patient's immune system. Dendritic cells express MHC class I and II, B7 costimulator, and IL-12, and are thus highly specialized antigen presenting cells. In prostate cancer, autologous dendritic cells pulsed with peptides of the prostate-specific membrane antigen (PSMA) are being used in a Phase I clinical trial to stimulate prostate cancer patients' immune systems (Tjoa et al., 1996, Prostate 28: 65–69; Murphy et al., 1996, Prostate 29: 371–380). Dendritic cells can be used to present PTAN peptides to T cells in the context of MHC class I and II molecules. In one embodiment, autologous dendritic cells are pulsed with PTAN peptides capable of binding to MHC molecules. In another embodiment, dendritic cells are pulsed with the complete PTAN protein. Yet another embodiment involves engineering the overexpression of the PTAN gene in dendritic cells using various implementing vectors known in the art, such as adenovirus (Arthur et al., 1997, Cancer Gene Ther. 4: 17–25), retrovirus (Henderson et al., 1996, Cancer Res. 56: 3763–3770), lentivirus, adeno-associated virus, DNA transfection (Ribas et al., 1997, Cancer Res. 57: 2865–2869), and tumor-derived RNA transfection (Ashley et al., 1997, J. Exp. Med. 186: 1177–1182). Cells expressing PTAN may also be engineered to express immune modulators, such as GM-CSF, and used as immunizing agents.

Anti-idiotypic anti-PTAN antibodies can also be used in anti-cancer therapy as a vaccine for inducing an immune response to cells expressing a PTAN protein. Specifically, the generation of anti-idiotypic antibodies is well known in the art and can readily be adapted to generate anti-idiotypic anti-PTAN antibodies that mimic an epitope on a PTAN protein (see, for example, Wagner et al., 1997, Hybridoma 16: 3340; Foon et al., 1995, J Clin Invest 96: 334–342; Herlyn et al., 1996, Cancer Immunol Immunother43: 65–76). Such an anti-idiotypic antibody can be used in cancer vaccine strategies.

Genetic immunization methods may be employed to generate prophylactic or therapeutic humoral and cellular immune responses directed against cancer cells expressing.PTAN. Constructs comprising DNA encoding a PTAN protein/immunogen and appropriate regulatory sequences may be injected directly into muscle or skin of an individual, such that the cells of the muscle or skin take-up the construct and express the encoded PTAN protein/immunogen. Expression of the PTAN protein immunogen results in the generation of prophylactic or therapeutic humoral and cellular immunity against prostate cancer. Various prophylactic and therapeutic genetic immunization techniques known in the art may be used (for review, see information and references published at Internet address www.genweb.com).

KITS

For use in the diagnostic and therapeutic applications described or suggested above, kits are also provided by the invention. Such kits may comprise a carrier means being compartmentalized to receive in close confinement one or more container means such as vials, tubes, and the like, each of the container means comprising one of the separate elements to be used in the method. For example, one of the container means may comprise a probe which is or can be detectably labeled. Such probe may be an antibody or polynucleotide specific for a PTAN protein or a PTAN gene or message, respectively. Where the kit utilizes nucleic acid hybridization to detect the target nucleic acid, the kit may also have containers containing nucleotide(s) for amplification of the target nucleic acid sequence and/or a container comprising a reporter-means, such as a biotin-binding protein, such as avidin or streptavidin, bound to a reporter molecule, such as an enzymatic, florescent, or radioisotope label.

EXAMPLES

Various aspects of the invention are further described and illustrated by way of the several examples which follow, none of which are intended to limit the scope of the invention.

Example 1

SSH-GENERATED ISOLATION OF cDNA FRAGMENT OF THE PTAN GENE

MATERIALS AND METHODS

LAPC Xenografts:

LAPC xenografts were obtained from Dr. Charles Sawyers (UCLA) and generated as described (Klein et al, 1997, Nature Med. 3: 402–408). Androgen dependent and independent LAPC-4 xenografts LAPC-4 AD and AI, respectively) and LAPC-9 AD xenografts were grown in male SCID mice and were passaged as small tissue chunks in recipient males. LAPC-4 AI xenografts were derived from LAPC-4 AD tumors. Male mice bearing LAPC4 AD tumors were castrated and maintained for 2–3 months. After the LAPC-4 tumors re-grew, the tumors were harvested and passaged in castrated males or in female SCID mice.

Cell Lines:

Human cell lines (e.g., HeLa) were obtained from the ATCC and were maintained in DMEM with 5% fetal calf serum.

RNA Isolation:

Tumor tissue and cell lines were homogenized in Trizol™ reagent (Life Technologies, Gibco BRL) using 10 ml/g tissue or 10 ml/$10^8$ cells to isolate total RNA. Poly A RNA was purified from total RNA using Qiagen's Oligotex™ mRNA Mini and Midi kits. Total and mRNA were quantified by spectrophotometric analysis (O.D. 260/280 nm) and analyzed by gel electrophoresis.

Oligonucleotides:

The following HPLC purified oligonucleotides were used.
DPNCDN (cDNA synthesis primer):
5'TTTTGATCAAGCTT$_{30}$3' (SEQ ID NO:9)
Adaptor 1:
5'CTAATACGACTCACTATAGGGCTC-GAGCGGCCGCCCGGGCAG3' (SEQ ID NO:10) 3'GGCCCGTCCTAG5' (SEQ ID NO:11)
Adaptor 2:
5'GTAATACGACTCACTATAGGGCAGCGTG-GTCGCGGCCGAG3' (SEQ ID NO:12) 3'CGGCTC-CTAG5' (SEQ ID NO:13)
PCR primer 1:
5'CTAATACGACTCACTATAGGGC3' (SEQ ID NO:14)
Nested primer (NP)1:
5'TCGAGCGGCCGCCCGGGCAGGA3' (SEQ ID NO:15)
Nested primer (NP)2:
5'AGCGTGGTCGCGGCCGAGGA3' (SEQ ID NO:16)

Suppression Subtractive Hybridization:

Suppression Subtractive Hybridization (SSH) was used to identify cDNAs corresponding to genes which may be differentially expressed in prostate cancer. The SSH reaction utilized cDNA from two different LAPC xenografts, subtracung LAPC-9 AD cDNA from LAPC-4 AD cDNA . The LAPC-4 AD xenograft was used as the source of the "tester" cDNA, while the LAPC-9 AD cDNA was used as the source of the "driver" cDNA.

Double stranded cDNAs corresponding to tester and driver cDNAs were synthesized from 2 μg of poly(A)$^+$ RNA isolated from the relevant xenograft tissue, as described above, using CLONTECH's PCR-Select cDNA Subtraction Kit and 1 ng of oligonucleotide DPNCDN as primer. First- and second-strand synthesis were carried out as described in the Kit's user manual protocol (CLONTECH Protocol No. PT1117–1, Catalog No. K1804-1). The resulting cDNA was digested with Dpn II for 3 hrs. at 37° C. Digested cDNA was extracted with phenol/chloroform (1:1) and ethanol precipitated.

Driver cDNA was generated by combining in a 1:1 ratio Dpn II digested cDNA from the relevant xenograft source (see above) with a mix of digested cDNAs derived from human benign prostatic hyperplasia (BPH), the human cell lines HeLa, 293, A431, Colo205, and mouse liver.

Tester cDNA was generated by diluting 1 μl of Dpn II digested cDNA from the relevant xenograft source (see above) (400 ng) in 5 μl of water. The diluted cDNA (2 μl, 160 ng) was then ligated to 2 μl of Adaptor 1 and Adaptor 2 (10 μM), in separate ligation reactions, in a total volume of 10 μl at 16° C. overnight, using 400 u of T4 DNA ligase (CLONTECH). Ligation was terminated with 1 μl of 0.2 M EDTA and heating at 72° C. for 5 min.

The first hybridization was performed by adding 1.5 μl (600 ng) of driver cDNA to each of two tubes containing 1.5 μl (20 ng) Adaptor 1- and Adaptor 2- ligated tester cDNA. In a final volume of 4 μl, the samples were overlaid with mineral oil, denatured in an MJ Research thermal cycler at 98° C. for 1.5 minutes, and then were allowed to hybridize for 8 hrs at 68° C. The two hybridizations were then mixed together with an additional 1 μl of fresh denatured driver cDNA and were allowed to hybridize overnight at 68° C. The second hybridization was then diluted in 200 μl of 20 mM Hepes, pH 8.3, 50 mM NaCl, 0.2 mM EDTA, heated at 70° C. for 7 min. and stored at −20° C.

PCR Amplification. Cloning and Sequencing of Gene Fragments Generated from SSH:

To amplify gene fragments resulting from SSH reactions, two PCR amplifications were performed. In the primary PCR reaction 1 μl of the diluted final hybridization mix was added to 1 μl of PCR primer 1 (10 μM), 0.5 μl dNTP mix (10 μM), 2.5 μl 10×reaction buffer (CLONTECH) and 0.5 μl 50×Advantage™ cDNA polymerase Mix (CLONTECH) in a final volume of 25 μl. PCR 1 was conducted using the following conditions: 75° C. for 5 min., 94° C. for 25 sec., then 27 cycles of 94° C. for 10 sec, 66° C. for 30 sec, 72° C. for 1.5 m primary PCR reactions were performed for each experiment. The products were pooled and diluted 1:10 with water. For the secondary PCR reaction, 1 μl from the pooled and diluted primary PCR reaction was added to the same reaction mix as used for PCR 1, except that primers NP1 and NP2 (10 μM) were used instead of PCR primer 1. PCR 2 was performed using 10–12 cycles of 94° C. for 10 sec, 68° C. for 30 sec, 72° C. for 1.5 minutes. The PCR products were analyzed using 2% agarose gel electrophoresis.

The PCR products were inserted into pCR2.1 using the T/A™ vector cloning kit (Invitrogen). Transformed E. coli were subjected to blue/white and ampicillin selection. White colonies were picked and arrayed into 96 well plates and were grown in liquid culture overnight. To identify inserts, PCR amplification was performed on 1 ml of bacterial culture using the conditions of PCR1 and NP1 and NP2 as primers. PCR products were analyzed using 2% agarose gel electrophoresis.

Bacterial clones were stored in 20% glycerol in a 96 well format. Plasmid DNA was prepared, sequenced, and subjected to nucleic acid homology searches of the GenBank, dBest, and NCI-CGAP databases.

RT-PCR Expression Analvsis: First strand cDNAs were generated from 1 μg of mRNA with oligo (dT)12–18 priming using the Gibco-BRL Superscript Preamplification system. The manufacturers protocol was used and included an incubation for 50 min at 42° C. with reverse transcriptase followed by RNAse H treatment at 37° C. for 20 min. After completing the reaction, the volume was increased to 200 μl with water prior to normalization. First strand cDNAs from 16 different normal human tissues were obtained from Clontech.

Normalization of the first strand cDNAs from multiple tissues was performed by using the primers 5'atatcgc-cgcgctcgtcgtcgacaa3' and 5'agccacacgcagctcattgtagaagg 3' to amplify β-actin. First strand cDNA (5 µl) was amplified in a total volume of 50 µl containing 0.4 µM primers, 0.2 µM each dNTPs, 1×PCR buffer (Clontech, 10 mM Tris-HCL, 1.5 mM MgCl$_2$, 50 mM KCl, pH8.3) and 1×Klentaq™ DNA polymerase (Clontech). Five µl of the PCR reaction was removed at 18, 20, and 22 cycles and used for agarose gel electrophoresis. PCR was performed using an MJ Research thermal cycler under the following conditions: initial denaturation was at 94° C. for 15 sec, followed by a 18, 20, and 22 cycles of 94° C. for 15, 65° C. for 2 min, 72° C. for 5 sec. A final extension at 72° C. was carried out for 2 min. After agarose gel electrophoresis, the band intensities of the 283 bp P-actin bands from multiple tissues were compared by visual inspection. Dilution factors for the first strand cDNAs were calculated to result in equal β-actin band intensities in all tissues after 22 cycles of PCR. Three rounds of normalization were required to achieve equal band intensities in all tissues after 22 cycles of PCR.

To determine expression levels of the PTAN gene, 5 µl of normalized first strand cDNA was analyzed by PCR using 25, 30, and 35 cycles of amplification using the following primer pairs, which were designed with the assistance of a program available on the web.

5'-TTG CAG TAG ATA GGT GGT CAG CTC C-3' (SEQ ID NO:19)

5'-CAA AGC AGA ATG TTT CAC CTC CA-3' (SEQ ID NO:20)

Semi quantitative expression analysis was achieved by comparing the PCR products at cycle numbers that give light band intensities.

RESULTS:

Two SSH experiments described in the Materials and Methods, supra, led to the isolation of numerous candidate gene fragment clones (SSH clones). All candidate clones were sequenced and subjected to homology analysis against all sequences in the major public gene and EST databases in order to provide information on the identity of the corresponding gene and to help guide the decision to analyze a particular gene for differential expression. In general, gene fragments which had no homology to any known sequence in any of the searched databases, and thus considered to represent novel genes, as well as gene fragments showing homology to previously sequenced expressed sequence tags (ESTs), were subjected to differential expression analysis by RT-PCR and/or Northern analysis.

One of the SHH clones comprising about 466 bp, showed significant homology to several testis-derived ESTs but no homology to any known gene, and was designated 26P5C7. The 26P5C7 sequence encodes a 125 amino acid open reading frame in its 5' end. The nucleotide and deduced ORF sequences of this SHH clone are shown in FIG. 4.

Differential expression analysis by RT-PCR showed some degree of over-expression in the LAPC-4 xenografts relative to normal prostate (FIG. 5A, Panel A). In addition, RT-PCR expression analysis of first strand cDNAs from 16 normal tissues showed a relatively testis-specific expression pattern in adult tissues, with lower level expression detectable in placenta, at 30 cycles of amplification.

Example 2

FULL LENGTH CLONING OF PTAN-1 AND PTAN-2

Full length cDNAs encoding two isoforms of the 26P5C7 gene were subsequently isolated from a testis library and designated PTAN-1 and PTAN-2. The nucleotide and amino acid sequences of PTAN-1 (GTD2) and PTAN-2 (GTC6) are shown in FIGS. 1 and 2, respectively. The open reading frames (ORFs) of PTAN-1 and PTAN-2 are identical with the exception of a 31 amino acid insertion at residues 45–76 in PTAN-1, resulting in a 434 amino acid ORF compared to a 403 amino acid ORF for PTAN-2. The PTAN-1 and PTAN-2 cDNAs were deposited on Nov. 5, 1998 with the American Type Culture Collection (ATCC; Manassas, Va.) as plasmids p26P5C7-GTD2 and p26P5C7-GTC6, respectively, and have been assigned Accession Nos. 98976 and 98977, respectively.

To confirm the presence of the 31 residue insert in PTAN-1, RT-PCR was performed on 1st strand cDNA derived from the LAPC-4 AD xenograft. PCR primers were designed within and outside of the insert region. The RT-PCR result confirmed that a cDNA containing the insert exists in the xenograft. Both PTAN-1 and PTAN-2 exhibit a putative nuclear localization signal at the amino terminus (residues 20–26). Using the PSORT program, the PTAN proteins are predicted to be nuclear in localization. The PTAN proteins have no homology to any known proteins, but the sequence does overlap with several ESTs derived from testis.

Example 3

FULL LENGTH CLONING OF PTAN-3

A full length cDNA encoding a third isoform of the 26P5C7 gene was isolated from a testis library and designated PTAN-3. The nucleotide and amino acid sequences of PTAN-3 (26P5C7-GTPIC8) are shown in FIG. 3. The PTAN-3 cDNA was deposited as plasmid p26P5C7-GTPIC8 with the American Type Culture Collection (ATCC; Manassas, Va.) on Feb. 12, 1999 as Accession No. 207095. An alignment of the amino acid sequences encoded by PTAN-1, PTAN-2, and PTAN-3 cDNAs (FIGS. 1, 2, and 3, respectively) is shown in FIG. 4. PTAN-3 is substantially identical to PTAN-1, except that it is truncated at the amino terminus (i.e., missing the first 56 amino acids of the PTAN-1 structure) and contains a 3 amino acid gap.

Example 4

PTAN GENE EXPRESSION ANALYSIS—TESTIS SPECIFIC IN NORMAL TISSUES

PTAN mRNA expression in normal human tissues was first analyzed by Northern blotting of two multiple tissue blots (Clontech; Palo Alto, Calif.), comprising a total of 16 different normal human tissues, using labeled 26P5C7 SSH fragment (Example 1) as a probe. RNA samples were quantitatively normalized with a β-actin probe. The results of this analysis are shown in FIG. 9. Expression of a 3 kb transcript was only detected in normal testis.

PTAN expression in normal tissues was further analyzed using a multi-tissue RNA dot blot containing 76 different samples (representing mainly normal tissues as well as a few cancer cell lines) demonstrated strong expression of PTAN only in testis (FIG. 10).

Example 5

PTAN EXPRESSION IN PROSTATE CANCER AND OTHER CANCERS

To analyze PTAN expression in cancer tissues and cell lines, Northern blot analysis was performed on RNA derived from the LAPC prostate cancer xenografts as well as a panel of prostate cancer and other cancer cell lines. The results (FIG. 11) show high levels of PTAN expression in LAPC4 AD and LAPC4 AI, with lower levels detected several cancer cell lines derived from breast (BT-20, DU4475). These results suggest that PTAN is a very testis specific gene that is up-regulated in prostate cancer and in breast cancer.

Example 6

GENERATION OF PTAN POLYCLONAL ANTIBODIES

To generate polyclonal antibodies directed against PTAN a 15 mer peptide was designed from a coding region common to all PTAN isoforms. The peptide CQAASDSSH-KIPISN (SEQ ID NO:21) was conjugated to keyhole limpet hemocyanin (KLH) and was used to immunize a rabbit.

Figure 12:
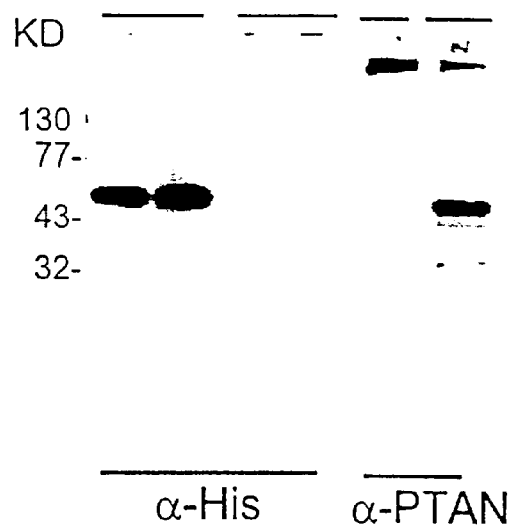
FIG. 12. Western blot detection of recombinant human PTAN-1 and PTAN-2 proteins in lysates of 293T cells transfected with a His-tagged PTAN-1 and PTAN-2 cDNAs using anti-PTAN rabbit polyclonal antiserum. Molecular weight standards are indicated on the side in kilodaltons (KD).

To test the rabbit serum for reactivity with PTAN proteins, full length PTAN-1 and PTAN-2 cDNAs were cloned into an expression vector that provides a 6His tag at the carboxyl-terminus (PCDNA 3.1 myc-his, InVitrogen). After transfection of the constructs into 293T cells, cell lysates were probed with anti-His antibody (Santa Cruz) and the anti-PTAN serum using Western blotting. Anti-His western blotting clearly shows expression of both PTAN-1 and PTAN-2, which migrate at the predicted molecular weights of 49 and 46 Kilodaltons (KD) respectively (FIG. 12).

Even though both gene isoforms were expressed using the same vector, expression of PTAN-1 was 10–20 fold higher than expression of PTAN-2. It is possible that PTAN-2 is less stable than PTAN-1 protein and that the additional sequence in PTAN-1 confers protein stability. The anti-PTAN antibody only recognized PTAN-1, even though the immunogen peptide sequence is present in both isoforms. This is probably due to the lower sensitivity of PTAN antibodies compared to anti-His and the lower expression level of PTAN-2. This polyclonal serum is specific for PTAN and may be used to assess the expression of PTAN in patient samples.

Example 7

PRODUCTION OF RECOMBINANT PTAN IN A MAMMALIAN SYSTEMS

To express recombinant PTAN-1 and PTAN-2, the full length PTAN-1 and PTAN-2 cDNAs were separately cloned into an expression vector that provides a 6His tag at the carboxyl-terminus (pCDNA 3.1 myc-his, InVitrogen). The constructs was transfected into 293T cells. Transfected 293T cell lysates were probed with the anti-PTAN polyclonal serum described in Example 5 above in a Western blot. The results show that the polyclonal serum recognizes a 49 and 46 kilodalton (KD) proteins only in the PTAN-1 and PTAN-2 transfected cells, respectively, and not in the control vector transfected cells (FIG. 12).

The PTAN genes were subcloned into the retroviral expression vector pSRαMSVtkneo and used to establish PTAN expressing cell lines as follows. The PTAN coding sequence (from translation initiation ATG to the termination codons) was amplified by PCR using ds cDNA template from PTAN cDNA. The PCR product was subcloned into pSRαMSVtkneo via the EcoR1(blunt-ended) and Xba 1 restriction sites on the vector and transformed into DH5α competent cells. Colonies were picked to screen for clones with unique internal restriction sites on the cDNA. The positive clone was confirmed by sequencing of the cDNA insert. Retroviruses were used for infection and generation of various cell lines using, for example, 3T3CL7, PC3, and LnCap cells.

Example 8

PRODUCTION OF RECOMBINANT PTAN IN A BACULOVIRUS SYSTEM

To generate a recombinant PTAN protein in a baculovirus expression system, the PTAN cDNA is cloned into the baculovirus transfer vector pBlueBac 4.5 (Invitrogen) which provides a His-tag at the N-terminus Specifically, pBlueBac-PTAN is co-transfected with helper plasmid pBac-N-Blue (Invitrogen) into SF9 (Spodoptera frugiperda) insect cells to generate recombinant baculovirus (see Invitrogen instruction manual for details). Baculovirus is then collected from cell supernatant and purified by plaque assay.

Recombinant PTAN protein is then generated by infection of HighFive insect cells (InVitrogen) with the purified baculovirus. Recombinant PTAN protein may be detected using anti-PTAN antibody. PTAN protein may be purified and used in various cell based assays or as immunogen to generate polyclonal and monoclonal antibodies specific for PTAN.

Example 9

CHROMOSOMAL MAPPING OF THE PTAN GENE

The chromosomal localization of PTAN was determined using the GeneBridge4 radiation hybrid panel (Walter et al., 1994, Nat. Genetics 7:22) (Research Genetics, Huntsville, Ala.). The following PCR primers were used to localize PTAN:

1. TCC AAT TCT TCC AGC AAT ATC CAC (SEQ ID NO:22)
2. AGG AAG TTG GGC CTG TTA CTG TTT (SEQ ID NO:23)

The resulting mapping vector for the 93 radiation hybrid panel DNAs was:
00010100010011000000000001000000110000101010100000001010000000001000000001011000000100000000001

This vector and a mapping program available on the web placed PTAN on chromosome 1q22.

Example 10

IDENTIFICATION OF POTENTIAL SIGNAL TRANSDUCTION PATHWAYS

To determine whether PTAN directly or indirectly activates known signal transduction pathways in cells, luciferase (luc) based transcriptional reporter assays are carried out in cells expressing PTAN. These transcriptional reporters contain consensus binding sites for known transcription factors which lie downstream of well characterized signal transduction pathways. The reporters and examples of there associated transcription factors, signal transduction pathways, and activation stimuli are listed below.

1. NFkB-luc, NFkB/Rel; Ik-kinase/SAPK; growth/apoptosis/stress
2. SRE-luc, SRF/TCF/ELK1; MAPK/SAPK; growth/differentiation
3. AP-1-luc, FOS/JUN; MAPK/SAPK/PKC; growth/apoptosis/stress
4. ARE-luc, androgen receptor; steroids/MAPK; growth/differentiation/apoptosis 5. p53-luc, p53; SAPK; growth/differentiation/apoptosis 6. CRE-luc, CREB/ATF2; PKA/p38; growth/apoptosis/stress PTAN-mediated effects may be assayed in cells showing mRNA expression. Luciferase reporter plasmids may be introduced by lipid mediated transfection (TFX-50, Promega). Luciferase activity, an indicator of relative transcriptional activity, is measured by incubation of cells extracts with luciferin substrate and luminescence of the reaction is monitored in a luminometer.

Example 11

GENERATION OF PTAN MONOCLONAL ANTIBODIES

In order to generate PTAN monoclonal antibodies, a glutathione-S-transferase (GST) fusion protein encompassing a PTAN protein is synthesized and used as immunogen. Balb C mice are initially immunized intraperitoneally with 200 μg of the GST-PTAN fusion protein mixed in complete Freund's adjuvant. Mice are subsequently immunized every 2 weeks with 75 μg of GST-PTAN protein mixed in Freund's incomplete adjuvant for a total of 3 immunizations. Reactivity of serum from immunized mice to full length PTAN protein is monitored by ELISA using a partially purified preparation of HIS-tagged PTAN protein expressed from 293T cells (Example 6). Mice showing the strongest reactivity are rested for 3 weeks and given a final injection of fusion protein in PBS and then sacrificed 4 days later. The spleens of the sacrificed mice are then harvested and fused to SPO/2 myeloma cells using standard procedures (Harlow and Lane, 1988). Supernatants from growth wells following HAT selection are screened by ELISA and Western blot to identify PTAN specific antibody producing clones.

The binding affinity of a PTAN monoclonal antibody may be determined using standard technology. Affinity measurements quantify the strength of antibody to epitope binding and may be used to help define which PTAN monoclonal antibodies are preferred for diagnostic or therapeutic use. The BLAcore™ system (Uppsala, Sweden) is a preferred method for determining binding affinity. The BLAcore™ system uses surface plasmon resonance (SPR, Welford K. 1991, Opt. Quant. Elect. 23:1; Morton and Myszka, 1998, Methods in Enzymology 295: 268) to monitor biomolecular interactions in real time. BIAcoreυ analysis conveniently generates association rate constants, dissociation rate constants, equilibrium dissociation constants, and affinity constants.

Example 12

IN VITRO ASSAYS OF PTAN FUNCTION

The expression of PTAN in prostate cancer and other cancers suggests a functional role in tumor progression. It is possible that PTAN functions as a transcription factor involved in activating genes involved in tumorigenesis or repressing genes that block tumorigenesis. PTAN function can be assessed in mammalian cells using in vitro approaches. For mammalian expression, PTAN can be cloned into a number of appropriate vectors, including pcDNA 3.1 myc-His-tag (Example 6) and the retroviral vector pSRatkneo (Muller et al., 1991, MCB 11:1785). Using such expression vectors, PTAN can be expressed in several cell lines, including PC-3, NIH 3T3, LNCaP and 293T. Expression of PTAN can be monitored using anti-PTAN antibodies (see Examples 5 and 10).

Mammalian cell lines expressing PTAN can be tested in several in vitro and in vivo assays, including cell proliferation in tissue culture, activation of apoptotic signals, tumor formation in SCID mice, and in vitro invasion using a membrane invasion culture system (MICS) (Welch et al. ,Int. J. Cancer 43: 449–457). PTAN cell phenotype is compared to the phenotype of cells that lack expression of PTAN.

Cell lines expressing PTAN can also be assayed for alteration of invasive and migratory properties by measuring passage of cells through a matrigel coated porous membrane chamber (Becton Dickinson). Passage of cells through the membrane to the opposite side is monitored using a fluorescent assay (Becton Dickinson Technical Bulletin #428) using calcein-Am (Molecular Probes) loaded indicator cells. Cell lines analyzed include parental and PTAN overexpressing PC3, 3T3 and LNCaP cells. To assay whether PTAN has chemoattractant properties, parental indicator cells are monitored for passage through the porous membrane toward a gradient of PTAN conditioned media compared to control media. This assay may also be used to qualify and quantify specific neutralization of the PTAN induced effect by candidate cancer therapeutic compositions.

Example 13

IN VIVO ASSAY FOR PTAN TUMOR GROWTH PROMOTION

The effect of the PTAN protein on tumor cell growth may be evaluated in vivo by gene overexpression in tumor-bearing mice. For example, SCID mice can be injected SQ on each flank with $1 \times 10^6$ of either PC3, TSUPR1, or DU145 cells containing tkNeo empty vector or PTAN. At least two strategies may be used: (1) Constitutive PTAN expression under regulation of an LTR promoter, and (2) Regulated expression under control of an inducible vector system, such as ecdysone, tet, etc. Tumor volume is then monitored at the appearance of palpable tumors and followed over time to determine if PTAN expressing cells grow at a faster rate. Additionally, mice may be implanted with $1 \times 10^5$ of the same cells orthotopically to determine if PTAN has an effect on local growth in the prostate or on the ability of the cells to metastasize, specifically to lungs, lymph nodes, and bone marrow.

The assay is also useful to determine the PTAN inhibitory effect of candidate therapeutic compositions, such as for example, PTAN intrabodies, PTAN antisense molecules and ribozymes.

Example 14

WESTERN ANALYSIS OF PTAN EXPRESSION IN SUBCELLULAR FRACTIONS

To determine the subcellular localization of PTAN, 293T cells were transfected with an expression vector encoding HIS-tagged PTAN (PCDNA 3.1 MYC/HIS, Invitrogen). The transfected cells were harvested and subjected to a differential subcellular fractionation protocol as previously described (Pemberton, P. A. et al, 1997, J of Histochemistry and Cytochemistry, 45:1697–1706.) This protocol separates the cell into fractions enriched for nuclei, heavy membranes (lysosomes, peroxisomes, and mitochondria), light membranes (plasma membrane and endoplasmic reticulum), and soluble proteins.

Figures 13A, 13B:
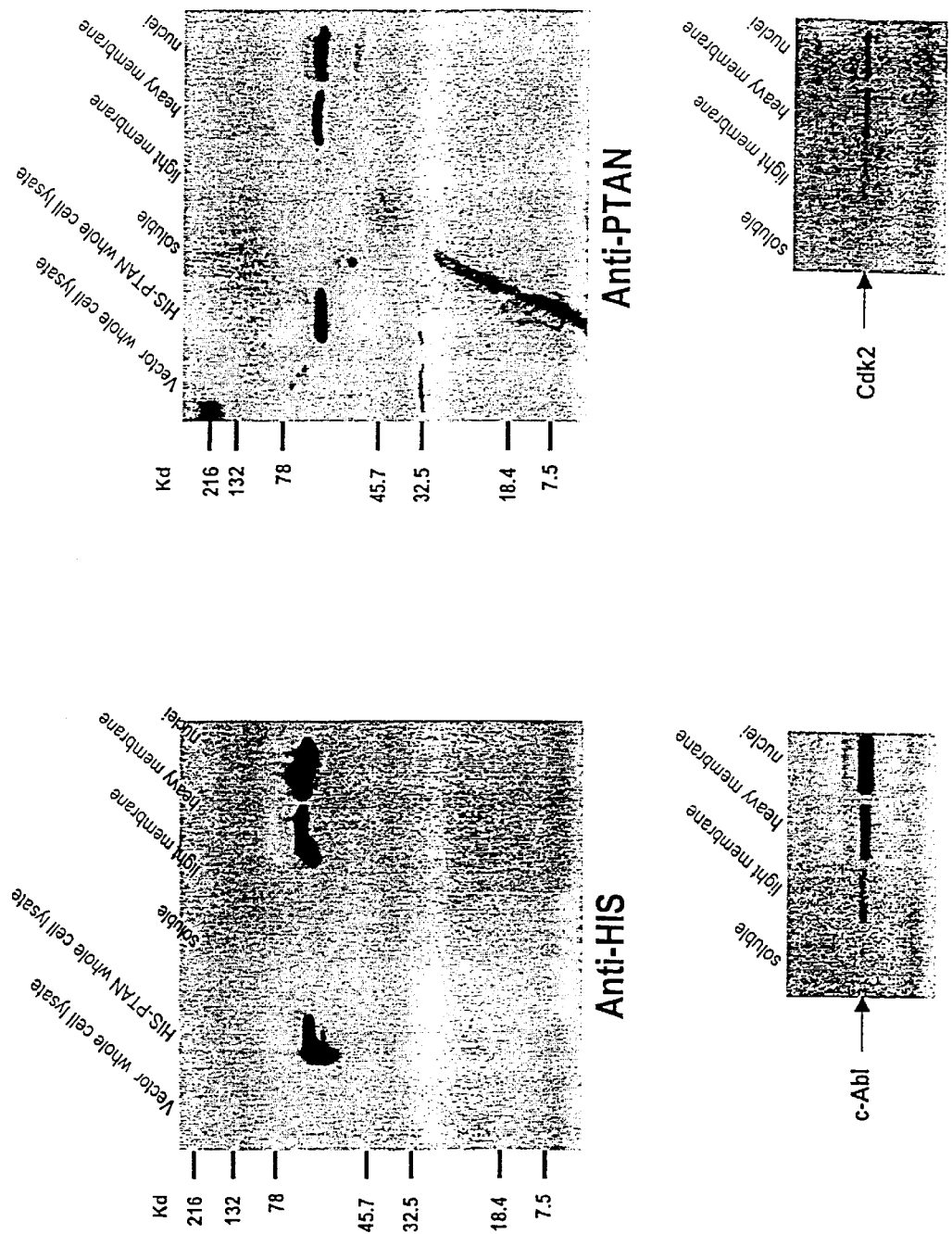
FIGS. 13(A–B). Western blot analysis of subcellular fractions of PTAN expressing 293T cells showing localization predominantly in the nuclear fraction of cells. Upper Left (FIG. 13A): Blot probed with 0.1 μg/ml of anti-His Ab. Upper Right (FIG. 13B): Blot probed with 1 μg/ml of affinity purified anti-PTAN polyclonal Ab. As controls for the enrichment of nuclear proteins in the nuclei fraction, the same lysates were analyzed by Western blot with antibodies specific for the nuclear proteins c-Abl (bottom left FIG. 13A) and Cdk2 (bottom right FIG. 13B ).

Western blot analysis of these fractions with either anti-HIS antibody or with anti-PTAN polyclonal antibody as probe demonstrates that PTAN localizes to the nuclear and heavy membrane fraction when overexpressed in 293T cells (FIG. 13). The blots were developed with species-specific HRP conjugated secondary Ab and visualized by enhanced chemiluminescense. The transfected cells were lysed in 2 mls of buffer and each subcellular fraction lane represents approximately $\frac{1}{160}^{th}$ (by volume) of the starting material. The whole cell lysate lane represents approximately $\frac{1}{160}^{th}$ of the starting material. Western analysis of the same subcellular fractions with antibodies to the nuclear proteins Cdk2 an c-Abl demonstrate co-localization of PTAN with these proteins to the same subcellular fractions.

This application claims the benefit of the filing dates of United States Provisional Patent Applications 06/129,518 filed Apr. 14, 1998, 06/113,229 filed Dec. 21, 1998 and 06/102,910 filed Oct. 2, 1998, and 60/102,556 filed Sep. 30, 1998 under the provisions of 35 USC 119(e), the contents of which are incorporated by reference herein in their entireties.

Throughout this application, various publications are referenced within parentheses. The disclosures of these publications are hereby incorporated by reference herein in their entireties.

The present invention is not to be limited in scope by the embodiments disclosed herein, which are intended as single illustrations of individual aspects of the invention, and any which are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

What is claimed is:

1. An isolated PTAN protein selected from the group consisting of (a) PTAN-1, having the amino acid sequence of (SEQ. ID. NO: 2);

(b) PTAN-2, having the amino acid sequence of (SEQ. ID. NO: 4), and (c) PTAN-3, having the amino acid sequence of (SEQ. ID. NO: 6).

2. An isolated peptide which consists of CQAASDSSH-KIPISN (SEQ. ID. NO: 21).

3. An immunogenic composition which composition comprises a PTAN protein of claim 1 and a physiologically acceptable carrier.

4. An immunogenic composition which composition comprises a polypeptide of claim 2 and a physiologically acceptable carrier.

5. A method to produce antibodies immunoreactive with a PTAN protein, which method comprises administering the composition of claim 3 to a mammalian host.

6. A method to produce antibodies immunoreactive with a PTAN protein, which method comprises administering the composition of claim 4 to a mammalian host.

* * * * *